(12) United States Patent
Furihata et al.

(10) Patent No.: US 12,370,466 B2
(45) Date of Patent: **\*Jul. 29, 2025**

(54) METHOD OF PURIFICATION AND PURIFIED PRODUCTS

(71) Applicant: Nissui Corporation, Tokyo (JP)

(72) Inventors: Kiyomi Furihata, Tokyo (JP); Masashi Katayama, Tokyo (JP)

(73) Assignee: Nissui Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/967,050

(22) Filed: Dec. 3, 2024

(65) Prior Publication Data

US 2025/0090978 A1 Mar. 20, 2025

Related U.S. Application Data

(63) Continuation of application No. 17/793,241, filed as application No. PCT/JP2022/007528 on Feb. 24, 2022, now Pat. No. 12,194,393.

(60) Provisional application No. 63/162,194, filed on Mar. 17, 2021.

(51) Int. Cl.
| | |
|---|---|
| *B01D 15/20* | (2006.01) |
| *B01D 15/32* | (2006.01) |
| *B01J 20/28* | (2006.01) |
| *B01J 20/287* | (2006.01) |
| *C07C 69/587* | (2006.01) |
| *G01N 30/52* | (2006.01) |
| *G01N 30/56* | (2006.01) |
| *C07C 67/56* | (2006.01) |

(52) U.S. Cl.
CPC ......... *B01D 15/206* (2013.01); *B01D 15/325* (2013.01); *B01J 20/28004* (2013.01); *B01J 20/287* (2013.01); *C07C 69/587* (2013.01); *G01N 30/52* (2013.01); *G01N 30/56* (2013.01); *B01J 2220/52* (2013.01); *C07C 67/56* (2013.01); *G01N 2030/565* (2013.01)

(58) Field of Classification Search
None
See application file for complete search history.

(56) References Cited

U.S. PATENT DOCUMENTS

| | | | |
|---|---|---|---|
| 5,840,944 A | 11/1998 | Furihata et al. | |
| 6,423,220 B1 | 7/2002 | Fex | |
| 6,923,907 B2 | 8/2005 | Hobbs et al. | |
| 8,778,187 B2 | 7/2014 | Gebauer | |

(Continued)

FOREIGN PATENT DOCUMENTS

| | | |
|---|---|---|
| CA | 1226249 A | 9/1987 |
| CN | 104302615 A | 1/2015 |

(Continued)

OTHER PUBLICATIONS

Machine translation of JP-2020537740-A, pp. 1-11. (Year: 2020).*

(Continued)

*Primary Examiner* — Clare M Perrin
(74) *Attorney, Agent, or Firm* — Foley & Lardner LLP

(57) ABSTRACT

In the specification, a method for purifying a compound by column chromatography, and a method for optimizing the symmetry factor and theoretical plate number by allowing the slurry to settle and reducing the sedimentation volume of the slurry. A compound purified by such method is also provided.

15 Claims, 2 Drawing Sheets

(56) References Cited

U.S. PATENT DOCUMENTS

| | | | |
|---|---|---|---|
| 9,321,793 B2* | 4/2016 | Larsen | C07F 7/20 |
| 10,188,964 B2 | 1/2019 | Witt et al. | |
| 2015/0126760 A1 | 5/2015 | Doisaki et al. | |
| 2016/0245782 A1 | 8/2016 | Nakano et al. | |
| 2017/0254729 A1 | 9/2017 | Pawliszyn et al. | |
| 2019/0113485 A1 | 4/2019 | Mao et al. | |
| 2020/0190431 A1* | 6/2020 | Doisaki | C11C 3/10 |
| 2020/0369982 A1 | 11/2020 | Kralovec et al. | |
| 2024/0075407 A1* | 3/2024 | Furihata | B01J 20/286 |

FOREIGN PATENT DOCUMENTS

| | | | |
|---|---|---|---|
| GB | 2 141 425 B | | 12/1984 |
| JP | H02-128693 A | | 5/1990 |
| JP | H05-222392 A | | 8/1993 |
| JP | H10-253609 A | | 9/1998 |
| JP | 2000-072713 A | | 3/2000 |
| JP | 2001-303089 A | | 10/2001 |
| JP | 2002-514492 A | | 5/2002 |
| JP | 2006-078231 A | | 3/2006 |
| JP | 2009-512840 A | | 3/2009 |
| JP | 2009-516194 A | | 4/2009 |
| JP | 2010-532470 A | | 10/2010 |
| JP | 2015-508179 A | | 3/2015 |
| JP | 2020537740 A | * | 12/2020 |
| WO | WO-2007/045491 A2 | | 4/2007 |
| WO | WO-2007/111390 A1 | | 10/2007 |
| WO | WO-2009/007321 A1 | | 1/2009 |
| WO | WO-2013/126405 A1 | | 8/2013 |
| WO | WO-2015/053276 A1 | | 4/2015 |
| WO | WO-2019/079159 A1 | | 4/2019 |
| WO | WO-2020/122167 A1 | | 6/2020 |

OTHER PUBLICATIONS

Asahi Glass Si-Tech, 2020 (accessed Jan. 12, 2024), "M.S. Gel," 10 pages.

Barth et al., "Chromatography Fundamentals, Part V: Theoretical Plates: Significance, Properties, and Uses," LCGC North America, 2018, 36:830-835.

Office Action dated Mar. 19, 2024 in CN 202280002680.3 with English machine translation.

Office Action issued on Aug. 15, 2023 in JP 2023-089885, with English machine translation.

Office Action issued on Jan. 5, 2023 in JP 2022-542132, with English machine translation.

Shimadzu et al., "Theoretical Plate Number and Symmetry Factor," https://www.shimadzu.con/an/service-support/technical-support/analysis-basics/basic/theoretical_plate.html, 2013 (accessed May 16, 2024), 2 pages.

Supplementary European Search Report dated May 10, 2024 in EP 22726378.7.

YMC, Preparative LC Systems Manual, Mar. 8, 2017, vol. 13, Chapter 15, p. 218, with English translation.

You can do it too! Lab scale column packing, cytiva newsletter [online], Feb. 24, 2009, https://www.cytivalifesciences.co.jp/newsletter/pure_protein/20090224_columnpacking.html, with English machine translation, 11 pages.

* cited by examiner

METHOD OF PURIFICATION AND PURIFIED PRODUCTS

CROSS-REFERENCE TO RELATED APPLICATIONS

This application is a Continuation of U.S. application Ser. No. 17/793,241, which is the U.S. National Stage of PCT/JP2022/007528, filed Feb. 24, 2022, which claims priority to U.S. Provisional Application No. 63/162,194, filed Mar. 17, 2021.

TECHNICAL FIELD

The present technology generally relates to methods of improving performance in column chromatography.

BACKGROUND ART

Chromatography is a purification method used in a broad range of industrial and research settings. Chromatography is used for quality control and preparative purposes in the food industry, environmental testing, and the pharmaceutical industry. Natural sources of chemicals offer plentiful sources of useful compounds, however extractions result in impure mixtures which often require further purification methods such as chromatography to isolate target chemicals. Due to similarity in chemical structures, mixtures of different compounds belonging to the same structural class prove challenging to purify and isolate specific compounds from. Methods of preparing columns and stationary phase to be used in chromatography can have drastic effects on the performance of the column and its ability to separate compounds having close structural similarity and similar interactions with the stationary and mobile phases. Methods for packing chromatography columns, such as sedimentation packing, high-pressure slurry packing and dry packing, are known as described in Patent Document 1. Sedimentation packing is a method in which a slurry of a packing material and liquid is inserted into a column, and settled to let the packaging material sediment. High-pressure slurry packing is a method in which a slurry of a packing material and liquid is inserted into a column, and liquid is delivered under high-pressure by the feed pump to let the packing material sediment. Dry packing is a method in which the packing material is inserted into the column as powder, then packed tightly using methods such as shaking the column, and subsequently degassing the packing material layer by feeding liquid. Patent Documents 2 and 3 describe methods for preparing a chromatography column by inserting the packing material as a slurry, and subsequently letting the packing material sediment and compressing the packing material. Non-Patent Document 1 describes a column packing method in a preparative liquid chromatography.

CITATION LIST

Patent Document

[Patent Document 1] Japanese Publication No. H10-253609
[Patent Document 2] WO 2015/053276
[Patent Document 3] Japanese Publication No. 2015-508179

Non-Patent Document

[Non-Patent Document 1] YMC15 Preparative LC System Manual SUMMARY OF INVENTION

Technical Problem

There is a need for methods of chromatography that will allow for the separation of similar compounds with similar retention times by increasing peak resolution, symmetry and theoretical plate number.

Solution to Problem

The present inventors discovered a method for purifying a compound by column chromatography and a method for optimizing the symmetry factor and theoretical plate number by allowing the slurry to stand and reducing the sedimentation volume of the slurry, and completed the present invention. The present invention is directed to a method of increasing the peak resolution, symmetry and theoretical plate number by allowing the slurry to stand for a predetermined length of time. The specification encompasses the following embodiments of the invention.

[1-1] A method of purifying one or more compounds by column chromatography comprising:
  adding a stationary phase to a column, and
  allowing a slurry comprising the stationary phase to settle in the column for a settling time.

[1-2] A method of packing a chromatography column comprising:
  adding a stationary phase to a column, and
  allowing a slurry comprising the stationary phase to settle in the column for a settling time.

[1-3] A method of increasing theoretical plate number (N) in a column chromatography comprising:
  adding a stationary phase to a column, and
  allowing a slurry comprising the stationary phase to settle in the column for a settling time, wherein the increase in N is relative to a column chromatography without settling time or wherein the increase in N is relative to a slurry that settles for a reduced settling time that is less than the settling time.

[1-4] A method of improving symmetry factor of a chromatographic peak in column chromatography comprising allowing a slurry to settle in the column for a settling time,
  wherein the improvement comprises decreasing the symmetry factor of the peak to a quantity $\geq 1$, and wherein the decrease is relative to a symmetry factor when a column chromatography comprises a reduced settling time that is absent or less than the settling time and the symmetry factor is $>1$; or
  the improvement comprises increasing the symmetry factor of the peak to a quantity $\leq 1$, and wherein the increase is relative to a symmetry factor when a column chromatography comprises a reduced settling time that is absent or less than the settling time and the symmetry factor is $<1$.

[1-5] The method of [1-4], wherein all chromatography conditions other than settling time are identical when the column chromatography comprises the settling time or when the column chromatography comprises the reduced settling time that is absent or less than the settling time.

[1-6] The method of any one of [1-1] to [1-5], wherein the column is under atmospheric pressure during settling time.

[1-7] The method of any one of [1-1] to [1-6], wherein pressure is applied to the column after settling time.

[1-8] The method of any one of [1-1] to [1-7], wherein each settling time is independently between about 0.5 minutes to about 5 minutes, about 5 minutes to about 10 minutes, about 10 minutes to about 15 minutes, about 15 minutes to about 20 minutes, about 20 minutes to about 25 minutes, about 25 minutes to about 30 minutes, about 30 minutes to about 35 minutes, about 35 minutes to about 40 minutes, about 40 minutes to about 45 minutes, about 45 minutes to about 50 minutes, about 50 minutes to about 55 minutes, about 55 minutes to about 60 minutes, about 60 minutes to about 65 minutes, about 65 minutes to about 70 minutes, about 70 minutes to about 75 minutes, about 75 minutes to about 80 minutes, about 80 minutes to about 85 minutes, about 85 minutes to about 90 minutes, about 90 minutes to about 95 minutes, or about 95 minutes to about 100 minutes, about 100 minutes to about 105 minutes, about 105 minutes to about 110 minutes, about 110 minutes to about 115 minutes, about 115 minutes to about 120 minutes.

[1-9] A method of purifying one or more compounds by column chromatography comprising decreasing sedimentation volume in a slurry, wherein the decrease in sedimentation volume is relative to the sedimentation volume of a fresh slurry.

[1-10] A method of packing a chromatography column comprising decreasing sedimentation volume in a slurry, wherein the decrease in sedimentation volume is relative to the sedimentation volume of a fresh slurry.

[1-11] A method of increasing theoretical plate number (N) in a column chromatography comprising decreasing sedimentation volume in a slurry, wherein the decrease in sedimentation volume is relative to a sedimentation volume of a fresh slurry, and wherein the increase in N is relative to an N of a column chromatography wherein the column is packed with the fresh slurry.

[1-12] A method of improving symmetry factor of a chromatographic peak in column chromatography comprising decreasing sedimentation volume in a slurry before column packing,
wherein the decrease in sedimentation volume is relative to the sedimentation volume of a fresh slurry, wherein the improvement comprises decreasing the symmetry factor of the peak to a quantity $\geq 1$ if the symmetry factor for the peak >1 when column chromatography is performed with a column packed with fresh slurry; or the improvement comprises increasing the symmetry factor of the peak to a quantity $\leq 1$ if the symmetry factor for the peak <1 when column chromatography is performed with a column packed with fresh slurry.

[1-13] The method of [1-12], wherein all chromatography conditions other than sedimentation volume are identical when the column chromatography comprises the decreased sedimentation volume or when the column chromatography is performed with a column packed with fresh slurry.

[1-14] The method of [1-12] or [1-13], wherein the fresh slurry comprises mobile phase and stationary phase combined for less than about 10 minutes, less than about 8 minutes, less than about 6 minutes, less than about 4 minutes, less than about 2 minutes, or less than about 1 minute.

[1-15] The method of any one of [1-9] to [1-14], wherein the decrease in sedimentation volume is over an amount of time between about 0 minutes to about 2 minutes, about 2 minutes to about 4 minutes, about 4 minutes to about 6 minutes, about 6 minutes to about 8 minutes, about 8 minutes to about 10 minutes, about 10 minutes to about 12 minutes, about 12 minutes to about 14 minutes, about 14 minutes to about 16 minutes, about 16 minutes to about 18 minutes, about 18 minutes to about 20 minutes, about 20 minutes to about 22 minutes, about 22 minutes to about 24 minutes, about 24 minutes to about 26 minutes, about 26 minutes to about 28 minutes, about 28 minutes to about 30 minutes, about 30 minutes to about 32 minutes, about 32 minutes to about 34 minutes, about 34 minutes to about 36 minutes, about 36 minutes to about 38 minutes, or about 38 minutes to about 40 minutes.

[1-16] The method of [1-15] wherein the sedimentation volume remains substantially constant after the amount of time.

[1-17] The method of any one of [1-9] to [1-16], wherein the decrease in sedimentation volume is over a settling time.

[1-18] The method of any one of [1-9] to [1-17], wherein decreasing sedimentation volume comprises allowing the mixture to settle at atmospheric pressure.

[1-19] The method of any one of [1-9] to [1-18], wherein pressure is applied to the column after the decrease in sedimentation volume.

[1-20] The method of any one of [1-1] to [1-18], wherein the column is an axial compression column.

[1-21] The method of any one of [1-1] to [1-20], wherein the slurry comprises a stationary phase and one or more of water, methanol, ethanol, acetonitrile, ethyl acetate, hexanes, or dichloromethane.

[1-22] The method of [1-21], wherein the slurry comprises methanol.

[1-23] The method of [1-21] or [1-22], wherein the stationary phase comprises an average particle size measured by laser diffraction scattering method of greater than 50 μm, greater than 45 μm, greater than 40 μm, greater than 35 μm, greater than 30 μm, greater than 25 μm, greater than 20 μm, greater than 15 μm, or greater than 10 μm.

[1-24] The method of [1-21] or [1-23], wherein the stationary phase comprises particles selected from at least one of C30, C22, C18, C8, C5, C4, biphenyl, fluorophenyl, hydrophilic interaction liquid chromatography (HILIC) stationary phase, acrylamide, silica, phenyl-hexyl stationary phase, polar embedded alkyl, and fluorophenyl propyl.

[1-25] The method of any one of [1-21] to [1-24], wherein the stationary phase comprises particles of C18.

[1-26] The method of any one of [1-1] to [1-25], wherein chromatography comprises elution with a mobile phase comprising one or more of water, methanol, ethanol, acetonitrile, ethyl acetate, hexanes, or dichloromethane.

[1-27] The method of [1-26], wherein the mobile phase comprises methanol.

[1-28] The method of any one of [1-1] to [1-27], wherein chromatography comprises a mobile phase comprising an additive selected from one or more of formic acid, ammonium formate, trimethylamine, ammonia, and ammonium hydroxide.

[1-29] The method of any one of [1-1] to [1-28], wherein column chromatography comprises a mobile phase gradient.

[1-30] The method of any one of [1-1] to [1-29], wherein chromatography comprises the purification of one or more analytes selected from fatty acids or esterified derivatives thereof, proteins, nucleic acids, and small molecules.

[1-31] The method of any one of [1-1] to [1-30], wherein chromatography comprises the purification of one or more fatty acids or an esterified derivative thereof.

[1-32] The method of [1-31], wherein the fatty acids are selected from one or more of docosahexaenoic acid, crotonic acid, myristoleic acid, palmitoleic acid, sapienic acid, oleic acid, elaidic acid, vaccenic acid, gadoleic acid, eicosenoic acid, erucic acid, nervonic acid, linoleic acid, eicosadienoic acid, docosadienoic acid, linolenic acid, pinolenic acid, eleostearic acid, mead acid, dihomo-γ-linolenic acid, eicosatrienoic acid, stearidonic acid, arachidonic acid, eicosatetraenoic acid, adrenic acid, bosseopentaenoic acid, eicosapentaenoic acid, ozubondo acid, sardine acid, tetracosanolpentaenoic acid, cervonic acid, herring acid, propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, carboceric acid, montanic acid, nonacosylic acid, melissic acid, hentriacontylic acid, lacceroic acid, psyllic acid, geddic acid, ceroplastic acid, hexatriacontylic acid, heptatriacontylic acid, octatriacontylic acid, nonatriacontylic acid, and tetracontylic acid.

[1-33] The method of [1-31] or [1-32], wherein the esterified derivative thereof is a methyl, ethyl, propyl, butyl, pentyl, hexyl, heptyl, octyl, nonyl, or decyl ester.

[1-34] The method of any one of [1-1] to [1-33], wherein chromatography comprises the purification of eicosapentaenoic acid ethyl ester and/or docosahexaenoic acid ethyl ester.

[1-35] The method of any one of [1-1] to [1-34], wherein the slurry is formed by:
  a) premixing stationary phase and mobile phase prior to addition of slurry to the column; or
  b) adding mobile phase to the column then adding stationary phase to the mobile phase.

[1-36] The method of [1-34], wherein the stationary phase is added to the mobile phase portion wise.

[1-37] A compound or composition purified by the method of any one of [1-1] to [1-36].

[1-38] The compound or composition of [1-37], wherein the compound is a fatty acid or esterified derivative thereof, protein, nucleic acid, or small molecule.

[1-39] The compound or composition of [1-37] or [1-38], wherein the compound is a fatty acid or an esterified derivative thereof.

[1-40] The compound or composition of [1-39], wherein the compound is docosahexaenoic acid, crotonic acid, myristoleic acid, palmitoleic acid, sapienic acid, oleic acid, elaidic acid, vaccenic acid, gadoleic acid, eicosenoic acid, erucic acid, nervonic acid, linoleic acid, eicosadienoic acid, docosadienoic acid, linolenic acid, pinolenic acid, eleostearic acid, mead acid, dihomo-γ-linolenic acid, eicosatrienoic acid, stearidonic acid, arachidonic acid, eicosatetraenoic acid, adrenic acid, bosseopentaenoic acid, eicosapentaenoic acid, ozubondo acid, sardine acid, tetracosanolpentaenoic acid, cervonic acid, herring acid, propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, carboceric acid, montanic acid, nonacosylic acid, melissic acid, hentriacontylic acid, lacceroic acid, psyllic acid, geddic acid, ceroplastic acid, hexatriacontylic acid, heptatriacontylic acid, octatriacontylic acid, nonatriacontylic acid, tetracontylic acid, or an esterified derivative thereof.

[1-41] The compound or composition of [1-39] or [1-40], wherein the esterified derivative thereof is a methyl, ethyl, propyl, butyl, pentyl, hexyl, heptyl, octyl, nonyl, or decyl ester.

[1-42] The compound or composition of any one of [1-37] to [1-41], wherein the compound is eicosapentaenoic acid ethyl ester and/or docosahexaenoic acid ethyl ester.

[1-43] The compound or composition of any one of [1-37] to [1-42], comprising a purity of greater than about 90%, greater than about 95%, greater than about 98%, greater than about 99%, greater than about 99.5%, greater than about 99.8%, or greater than about 99.9%.

[1-44] The compound or composition of any one of [1-36] to [1-43], comprising a yield of greater than 50%, greater than 55%, greater than 60%, greater than 65%, greater than 70%, greater than 75%, or greater than 80%.

[1-45] The compound or composition of any one of [1-36] to [1-43], comprising a recovery rate of greater than 55%, greater than 60%, greater than 65%, greater than 70%, greater than 75%, greater than 80%, greater than 85%, greater than 90%, greater than 95%, greater than 98%, greater than 99%, or greater than 99.7%.

[1-46] The compound or composition of [1-42] wherein eicosapentaenoic acid ethyl ester and docosahexaenoic acid ethyl ester obtained by purification is contained at a content of equal to or greater than about 80%, equal to or greater than about 85%, equal to or greater than about 86%, equal to or greater than about 90%, equal to or greater than about 95%, equal to or greater than about 96.5%, equal to or greater than about 98%, equal to or greater than about 99%, equal to or greater than about 99.5%, equal to or greater than about 99.8%, or g equal to or greater than about 99.9%.

[1-47] The compound or composition of [1-42] wherein eicosapentaenoic acid ethyl ester or docosahexaenoic acid ethyl ester obtained by purification is contained at a content of equal to or greater than about 80%, equal to or greater than about 85%, equal to or greater than about 86%, equal to or greater than about 90%, equal to or greater than about 95%, equal to or greater than about 96.5%, equal to or greater than about 98%, equal to or greater than about 99%, equal to or greater than about 99.5%, equal to or greater than about 99.8%, or g equal to or greater than about 99.9%.

[2-1] A method of purifying one or more compounds by column chromatography comprising:
  preparing a slurry containing a stationary phase in liquid,
  allowing the slurry to stand in the column for a standing time to allow the stationary phase to settle,
  applying a packing pressure to the settled stationary phase to form a packed layer of stationary phase, and
  performing column chromatography using a column containing the packed layer of stationary phase.

[2-2] A method of packing a chromatography column comprising:
  preparing a slurry containing a stationary phase in liquid,
  allowing the slurry to stand in the column for a staning time to allow the stationary phase to settle, and
  applying a packing pressure to the settled stationary phase to form a packed layer of stationary phase.

[2-3] A method of increasing theoretical plate number (N) in a column chromatography comprising:
  preparing a slurry containing a stationary phase in liquid,
  allowing the slurry to stand in the column for a standing time to allow the stationary phase to settle,
  applying a packing pressure to the settled stationary phase to form a packed layer of stationary phase, wherein the increase in N is relative to a column chromatography in which a slurry was not allowed to stand or a slurry was allowed to stand for a reduced standing time that is less than the standing time.

[2-4] A method of improving symmetry factor of a chromatographic peak in column chromatography comprising:
preparing a slurry containing a stationary phase in liquid,
allowing the slurry to stand in the column for a standing time to allow the stationary phase to settle,
applying a packing pressure to the settled stationary phase to form a packed layer of stationary phase
wherein the improvement comprises decreasing the symmetry factor of the peak to a quantity ≥1, and wherein the decrease is relative to a symmetry factor of a column chromatography in which a slurry was not allowed to stand or a slurry was allowed to stand for a reduced standing time that is less than the standing time and the symmetry factor is >1; or
the improvement comprises increasing the symmetry factor of the peak to a quantity ≤1, and wherein the increase is relative to a symmetry factor of a column chromatography in which a slurry was not allowed to stand or a slurry was allowed to stand for a reduced standing time that is less than the standing time and the symmetry factor is <1.

[2-5] The method of [2-4], wherein all chromatography conditions other than standing time are identical to a column chromatography in which a slurry was not allowed to stand or a slurry was allowed to stand for a reduced standing time that is less than the standing time.

[2-6] The method of any one of [2-1] to [2-5], wherein the column is under atmospheric pressure during the standing time.

[2-7] The method of any one of [2-1] to [2-6], wherein the standing time is between about 0.5 minutes to about 5 minutes, about 5 minutes to about 10 minutes, about 10 minutes to about 15 minutes, about 15 minutes to about 20 minutes, about 20 minutes to about 25 minutes, about 25 minutes to about 30 minutes, about 30 minutes to about 35 minutes, about 35 minutes to about 40 minutes, about 40 minutes to about 45 minutes, about 45 minutes to about 50 minutes, about 50 minutes to about 55 minutes, about 55 minutes to about 60 minutes, about 60 minutes to about 65 minutes, about 65 minutes to about 70 minutes, about 70 minutes to about 75 minutes, about 75 minutes to about 80 minutes, about 80 minutes to about 85 minutes, about 85 minutes to about 90 minutes, about 90 minutes to about 95 minutes, or about 95 minutes to about 100 minutes, about 100 minutes to about 105 minutes, about 105 minutes to about 110 minutes, about 110 minutes to about 115 minutes, about 115 minutes to about 120 minutes.

[2-8] A method of any one of [2-1] to [2-7], wherein allowing the slurry to stand results in a decrease of a volume of a packed layer of stationary phase relative to a volume of a packed layer of stationary phase in a column chromatography in which the slurry was not allowed to stand.

[2-9] The method of [2-8], comprising liquid and a stationary phase that were agitated for less than about 10 minutes, less than about 8 minutes, less than about 6 minutes, less than about 4 minutes, less than about 2 minutes, or less than about 1 minute when preparing the slurry.

[2-10] The method of any one of [2-1] to [2-9], wherein the column is an axial compression column.

[2-11] The method of any one of [2-1] to [2-10], wherein the slurry comprises a stationary phase and one or more of water, methanol, ethanol, acetonitrile, ethyl acetate, hexanes, or dichloromethane.

[2-12] The method of [2-11], wherein the slurry comprises methanol. [2-13] The method of [2-11] or [2-12], wherein the stationary phase comprises particles having a median particle diameter measured by laser diffraction scattering method of greater than 50 μm, greater than 45 μm, greater than 40 μm, greater than 35 μm, greater than 30 μm, greater than 25 μm, greater than 20 μm, greater than 15 μm, or greater than 10 μm.

[2-14] The method of [2-11] or [2-13], wherein the stationary phase comprises particles selected from at least one of C30, C22, C18, C8, C5, C4, biphenyl, fluorophenyl, hydrophilic interaction liquid chromatography (HILIC) stationary phase, acrylamide, silica, phenyl-hexyl stationary phase, polar embedded alkyl, and fluorophenyl propyl.

[2-15] The method of any one of [2-11] to [2-14], wherein the stationary phase comprises particles of C18.

[2-16] The method of any one of [2-1] to [2-15], wherein a slurry concentration is from about 20% to about 70%, preferably from about 30% to about 70%, and more preferably from about 30% to about 60%.

[2-17] The method of any one of [2-1] to [2-16], wherein chromatography comprises elution with a mobile phase comprising one or more of water, methanol, ethanol, acetonitrile, ethyl acetate, hexanes, dichloromethane or supercritical carbon dioxide.

[2-18] The method of [2-17], wherein the mobile phase comprises methanol.

[2-19] The method of any one of [2-1] to [2-18], wherein chromatography comprises a mobile phase comprising an additive selected from one or more of formic acid, ammonium formate, trimethylamine, ammonia, and ammonium hydroxide.

[2-20] The method of any one of [2-1] to [2-19], wherein column chromatography comprises a mobile phase gradient.

[2-21] The method of any one of [2-1] to [2-20], wherein chromatography comprises the purification of one or more analytes selected from fatty acids or esterified derivatives thereof, proteins, nucleic acids, and small molecules.

[2-22] The method of any one of [2-1] to [2-21], wherein chromatography comprises the purification of one or more fatty acids or an esterified derivative thereof.

[2-23] The method of [2-22], wherein the fatty acids are selected from one or more of docosahexaenoic acid, crotonic acid, myristoleic acid, palmitoleic acid, sapienic acid, oleic acid, elaidic acid, vaccenic acid, gadoleic acid, eicosenoic acid, erucic acid, nervonic acid, linoleic acid, eicosadienoic acid, docosadienoic acid, linolenic acid, pinolenic acid, eleostearic acid, mead acid, dihomo-γ-linolenic acid, eicosatrienoic acid, stearidonic acid, arachidonic acid, eicosatetraenoic acid, adrenic acid, bosseopentaenoic acid, eicosapentaenoic acid, ozubondo acid, sardine acid, tetracosanolpentaenoic acid, cervonic acid, herring acid, propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, carboceric acid, montanic acid, nonacosylic acid, melissic acid, hentriacontylic acid, lacceroic acid, psyllic acid, geddic acid, ceroplastic acid, hexatriacontylic acid, heptatriacontylic acid, octatriacontylic acid, nonatriacontylic acid, and tetracontylic acid.

[2-24] The method of [2-21] or [2-22], wherein the esterified derivative thereof is a methyl, ethyl, propyl, butyl, pentyl, hexyl, heptyl, octyl, nonyl, or decyl ester.

[2-25] The method of any one of [2-1] to [2-24], wherein chromatography comprises the purification of eicosapentaenoic acid ethyl ester and/or docosahexaenoic acid ethyl ester.

[2-26] The method of any one of [2-1] to [2-25], wherein the slurry is formed by:
   a) premixing stationary phase and liquid prior to addition of the slurry to the column; or
   b) adding liquid to the column then adding stationary phase to the liquid.

[2-27] The method of [2-26], wherein the stationary phase is added to the liquid portion wise.

[2-28] A compound or a composition comprising the compound purified by the method of any one of [2-1] to [2-27].

[2-29] The compound or composition of [2-28], wherein the compound is a fatty acid or esterified derivative thereof, protein, nucleic acid, or small molecule.

[2-30] The compound or composition of [2-28] or [2-29], wherein the compound is a fatty acid or an esterified derivative thereof.

[2-31] The compound or composition of [2-30], wherein the compound is docosahexaenoic acid, crotonic acid, myristoleic acid, palmitoleic acid, sapienic acid, oleic acid, elaidic acid, vaccenic acid, gadoleic acid, eicosenoic acid, erucic acid, nervonic acid, linoleic acid, eicosadienoic acid, docosadienoic acid, linolenic acid, pinolenic acid, eleostearic acid, mead acid, dihomo-γ-linolenic acid, eicosatrienoic acid, stearidonic acid, arachidonic acid, eicosatetraenoic acid, adrenic acid, bosseopentaenoic acid, eicosapentaenoic acid, ozubondo acid, sardine acid, tetracosanolpentaenoic acid, cervonic acid, herring acid, propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, carboceric acid, montanic acid, nonacosylic acid, melissic acid, hentriacontylic acid, lacceroic acid, psyllic acid, geddic acid, ceroplastic acid, hexatriacontylic acid, heptatriacontylic acid, octatriacontylic acid, nonatriacontylic acid, tetracontylic acid, or an esterified derivative thereof.

[2-32] The compound or composition of [2-30] or [2-31], wherein the esterified derivative thereof is a methyl, ethyl, propyl, butyl, pentyl, hexyl, heptyl, octyl, nonyl, or decyl ester.

[2-33] The compound or composition of any one of [2-28] to [2-32], wherein the compound is eicosapentaenoic acid ethyl ester and/or docosahexaenoic acid ethyl ester.

[2-34] The compound or composition of any one of [2-28] to [2-33], comprising a purity of equal to or greater than about 80%, equal to or greater than about 85%, equal to or greater than about 86%, equal to or greater than about 90%, equal to or greater than about 95%, equal to or greater than about 96.5%, equal to or greater than about 98%, equal to or greater than about 99%, equal to or greater than about 99.5%, equal to or greater than about 99.8%, or g equal to or greater than about 99.9%.

[2-35] The compound or composition of [2-33] wherein eicosapentaenoic acid ethyl ester and docosahexaenoic acid ethyl ester obtained by purification is contained at a content of equal to or greater than about 80%, equal to or greater than about 85%, equal to or greater than about 86%, equal to or greater than about 90%, equal to or greater than about 95%, equal to or greater than about 96.5%, equal to or greater than about 98%, equal to or greater than about 99%, equal to or greater than about 99.5%, equal to or greater than about 99.8%, or g equal to or greater than about 99.9%.

[2-36] The compound or composition of [2-33] wherein eicosapentaenoic acid ethyl ester or docosahexaenoic acid ethyl ester obtained by purification is contained at a content of equal to or greater than about 80%, equal to or greater than about 85%, equal to or greater than about 86%, equal to or greater than about 90%, equal to or greater than about 95%, equal to or greater than about 96.5%, equal to or greater than about 98%, equal to or greater than about 99%, equal to or greater than about 99.5%, equal to or greater than about 99.8%, or g equal to or greater than about 99.9%.

[3-1] A method of purifying one or more compounds by column chromatography comprising:
   adding a stationary phase to a column, and
   allowing a slurry comprising the stationary phase to stand in the column for a standing time.

[3-2] A method of packing a chromatography column comprising:
   adding a stationary phase to a column, and
   allowing a slurry comprising the stationary phase to stand in the column for a standing time.

[3-3] A method of increasing theoretical plate number (N) in a column chromatography comprising:
   adding a stationary phase to a column, and
   allowing a slurry comprising the stationary phase to stand in the column for a standing time, wherein the increase in N is relative to a column chromatography without standing time or wherein the increase in Nis relative to a slurry that stands for a reduced standing time that is less than the standing time.

[3-4] A method of improving symmetry factor of a chromatographic peak in column chromatography comprising allowing a slurry to stand in the column for a standing time,
   wherein the improvement comprises decreasing the symmetry factor of the peak to a quantity ≥1, and wherein the decrease is relative to a symmetry factor when a column chromatography comprises a reduced standing time that is absent or less than the standing time and the symmetry factor is >1; or
   the improvement comprises increasing the symmetry factor of the peak to a quantity ≤1, and wherein the increase is relative to a symmetry factor when a column chromatography comprises a reduced standing time that is absent or less than the standing time and the symmetry factor is <1.

[3-5] The method of [3-4], wherein all chromatography conditions other than standing time are identical when the column chromatography comprises the standing time or when the column chromatography comprises the reduced standing time that is absent or less than the standing time.

[3-6] The method of any one of [3-1] to [3-5], wherein the column is under atmospheric pressure during standing time.

[3-7] The method of any one of [3-1] to [3-6], wherein pressure is applied to the column after standing time.

[3-8] The method of any one of [3-1] to [3-7], wherein each standing time is independently between about 0.5 minutes to about 5 minutes, about 5 minutes to about 10 minutes, about 10 minutes to about 15 minutes, about 15 minutes to about 20 minutes, about 20 minutes to about 25 minutes, about 25 minutes to about 30 minutes, about 30 minutes to about 35 minutes, about 35 minutes to about 40 minutes, about 40 minutes to about 45 minutes, about 45 minutes to about 50 minutes, about 50 minutes to about 55 minutes, about 55 minutes to about 60 minutes, about 60 minutes to about 65 minutes, about 65 minutes to about 70 minutes, about 70 minutes to about 75 minutes, about 75 minutes to about 80 minutes, about 80 minutes to about 85 minutes, about 85 minutes to about 90 minutes, about 90 minutes to about 95 minutes, or about 95 minutes to about 100 minutes, about 100 minutes to about 105 minutes, about 105 minutes to about 110 minutes, about 110 minutes to about 115 minutes, about 115 minutes to about 120 minutes.

[3-9] A method of purifying one or more compounds by column chromatography comprising decreasing sedimentation volume in a slurry, wherein the decrease in sedimentation volume is relative to the sedimentation volume of a fresh slurry.

[3-10] A method of packing a chromatography column comprising decreasing sedimentation volume in a slurry, wherein the decrease in sedimentation volume is relative to the sedimentation volume of a fresh slurry.

[3-11] A method of increasing theoretical plate number (N) in a column chromatography comprising decreasing sedimentation volume in a slurry, wherein the decrease in sedimentation volume is relative to a sedimentation volume of a fresh slurry, and wherein the increase in Nis relative to an N of a column chromatography wherein the column is packed with the fresh slurry.

[3-12] A method of improving symmetry factor of a chromatographic peak in column chromatography comprising decreasing sedimentation volume in a slurry before column packing,
  wherein the decrease in sedimentation volume is relative to the sedimentation volume of a fresh slurry, wherein the improvement comprises decreasing the symmetry factor of the peak to a quantity ≥1 if the symmetry factor for the peak >1 when column chromatography is performed with a column packed with fresh slurry; or
  the improvement comprises increasing the symmetry factor of the peak to a quantity ≤1 if the symmetry factor for the peak <1 when column chromatography is performed with a column packed with fresh slurry.

[3-13] The method of [3-12], wherein all chromatography conditions other than sedimentation volume are identical when the column chromatography comprises the decreased sedimentation volume or when the column chromatography is performed with a column packed with fresh slurry.

[3-14] The method of [3-12] or [3-13], wherein the fresh slurry comprises mobile phase and stationary phase combined for less than about 10 minutes, less than about 8 minutes, less than about 6 minutes, less than about 4 minutes, less than about 2 minutes, or less than about 1 minute.

[3-15] The method of any one of [3-9] to [3-14], wherein the decrease in sedimentation volume is over an amount of time between about 0 minutes to about 2 minutes, about 2 minutes to about 4 minutes, about 4 minutes to about 6 minutes, about 6 minutes to about 8 minutes, about 8 minutes to about 10 minutes, about 10 minutes to about 12 minutes, about 12 minutes to about 14 minutes, about 14 minutes to about 16 minutes, about 16 minutes to about 18 minutes, about 18 minutes to about 20 minutes, about 20 minutes to about 22 minutes, about 22 minutes to about 24 minutes, about 24 minutes to about 26 minutes, about 26 minutes to about 28 minutes, about 28 minutes to about 30 minutes, about 30 minutes to about 32 minutes, about 32 minutes to about 34 minutes, about 34 minutes to about 36 minutes, about 36 minutes to about 38 minutes, or about 38 minutes to about 40 minutes.

[3-16] The method of [3-15] wherein the sedimentation volume remains substantially constant after the amount of time.

[3-17] The method of any one of [3-9] to [3-16], wherein the decrease in sedimentation volume is over a standing time.

[3-18] The method of any one of [3-9] to [3-17], wherein decreasing sedimentation volume comprises allowing the mixture to stand at atmospheric pressure.

[3-19] The method of any one of [3-9] to [3-18], wherein pressure is applied to the column after the decrease in sedimentation volume.

[3-20] The method of any one of [3-1] to [3-18], wherein the column is an axial compression column.

[3-21] The method of any one of [3-1] to [3-20], wherein the slurry comprises a stationary phase and one or more of water, methanol, ethanol, acetonitrile, ethyl acetate, hexanes, or dichloromethane.

[3-22] The method of [3-21], wherein the slurry comprises methanol.

[3-23] The method of [3-21] or [3-22], wherein the stationary phase comprises an average particle size measured by laser diffraction scattering method of greater than 50 µm, greater than 45 µm, greater than 40 µm, greater than 35 µm, greater than 30 µm, greater than 25 µm, greater than 20 µm, greater than 15 µm, or greater than 10 µm.

[3-24] The method of [3-21] or [3-23], wherein the stationary phase comprises particles selected from at least one of C30, C22, C18, C8, C5, C4, biphenyl, fluorophenyl, hydrophilic interaction liquid chromatography (HILIC) stationary phase, acrylamide, silica, phenyl-hexyl stationary phase, polar embedded alkyl, and fluorophenyl propyl.

[3-25] The method of any one of [3-21] to [3-24], wherein the stationary phase comprises particles of C18.

[3-26] The method of any one of [3-1] to [3-25], wherein chromatography comprises elution with a mobile phase comprising one or more of water, methanol, ethanol, acetonitrile, ethyl acetate, hexanes, or dichloromethane.

[3-27] The method of [3-26], wherein the mobile phase comprises methanol.

[3-28] The method of any one of [3-1] to [3-27], wherein chromatography comprises a mobile phase comprising an additive selected from one or more of formic acid, ammonium formate, trimethylamine, ammonia, and ammonium hydroxide.

[3-29] The method of any one of [3-1] to [3-28], wherein column chromatography comprises a mobile phase gradient.

[3-30] The method of any one of [3-1] to [3-29], wherein chromatography comprises the purification of one or more analytes selected from fatty acids or esterified derivatives thereof, proteins, nucleic acids, and small molecules.

[3-31] The method of any one of [3-1] to [3-30], wherein chromatography comprises the purification of one or more fatty acids or an esterified derivative thereof.

[3-32] The method of [3-31], wherein the fatty acids are selected from one or more of docosahexaenoic acid, crotonic acid, myristoleic acid, palmitoleic acid, sapienic acid, oleic acid, elaidic acid, vaccenic acid, gadoleic acid, eicosenoic acid, erucic acid, nervonic acid, linoleic acid, eicosadienoic acid, docosadienoic acid, linolenic acid, pinolenic acid, eleostearic acid, mead acid, dihomo-γ-linolenic acid, eicosatrienoic acid, stearidonic acid, arachidonic acid, eicosatetraenoic acid, adrenic acid, bosseopentaenoic acid, eicosapentaenoic acid, ozubondo acid, sardine acid, tetracosanolpentaenoic acid, cervonic acid, herring acid, propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, carboceric acid, montanic acid, nonacosylic acid, melissic acid, hentriacontylic acid, lacceroic acid, psyllic acid, geddic acid, ceroplastic acid, hexatriacontylic acid, heptatriacontylic acid, octatriacontylic acid, nonatriacontylic acid, and tetracontylic acid.

[3-33] The method of [3-31] or [3-32], wherein the esterified derivative thereof is a methyl, ethyl, propyl, butyl, pentyl, hexyl, heptyl, octyl, nonyl, or decyl ester.

[3-34] The method of any one of [3-1] to [3-33], wherein chromatography comprises the purification of eicosapentaenoic acid ethyl ester and/or docosahexaenoic acid ethyl ester.

[3-35] The method of any one of [3-1] to [3-34], wherein the slurry is formed by:
 a) premixing stationary phase and mobile phase prior to addition of slurry to the column; or
 b) adding mobile phase to the column then adding stationary phase to the mobile phase.

[3-36] The method of [3-34], wherein the stationary phase is added to the mobile phase portion wise.

[3-37] A compound or composition purified by the method of any one of [3-1] to [3-36].

[3-38] The compound or composition of [3-37], wherein the compound is a fatty acid or esterified derivative thereof, protein, nucleic acid, or small molecule.

[3-39] The compound or composition of [3-37] or [3-38], wherein the compound is a fatty acid or an esterified derivative thereof.

[3-40] The compound or composition of [3-39], wherein the compound is docosahexaenoic acid, crotonic acid, myristoleic acid, palmitoleic acid, sapienic acid, oleic acid, elaidic acid, vaccenic acid, gadoleic acid, eicosenoic acid, erucic acid, nervonic acid, linoleic acid, eicosadienoic acid, docosadienoic acid, linolenic acid, pinolenic acid, eleostearic acid, mead acid, dihomo-γ-linolenic acid, eicosatrienoic acid, stearidonic acid, arachidonic acid, eicosatetraenoic acid, adrenic acid, bosseopentaenoic acid, eicosapentaenoic acid, ozubondo acid, sardine acid, tetracosanolpentaenoic acid, cervonic acid, herring acid, propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, carboceric acid, montanic acid, nonacosylic acid, melissic acid, hentriacontylic acid, lacceroic acid, psyllic acid, geddic acid, ceroplastic acid, hexatriacontylic acid, heptatriacontylic acid, octatriacontylic acid, nonatriacontylic acid, tetracontylic acid, or an esterified derivative thereof.

[3-41] The compound or composition of [3-39] or [3-40], wherein the esterified derivative thereof is a methyl, ethyl, propyl, butyl, pentyl, hexyl, heptyl, octyl, nonyl, or decyl ester.

[3-42] The compound or composition of any one of [3-37] to [3-41], wherein the compound is eicosapentaenoic acid ethyl ester and/or docosahexaenoic acid ethyl ester.

[3-43] The compound or composition of any one of [3-37] to [3-42], comprising a purity of equal to or greater than about 80%, equal to or greater than about 85%, equal to or greater than about 86%, equal to or greater than about 90%, equal to or greater than about 95%, equal to or greater than about 96.5%, equal to or greater than about 98%, equal to or greater than about 99%, equal to or greater than about 99.5%, equal to or greater than about 99.8%, or g equal to or greater than about 99.9%.

[3-44] The compound or composition of [3-42] wherein eicosapentaenoic acid ethyl ester and docosahexaenoic acid ethyl ester obtained by purification is contained at a content of equal to or greater than about 80%, equal to or greater than about 85%, equal to or greater than about 86%, equal to or greater than about 90%, equal to or greater than about 95%, equal to or greater than about 96.5%, equal to or greater than about 98%, equal to or greater than about 99%, equal to or greater than about 99.5%, equal to or greater than about 99.8%, or g equal to or greater than about 99.9%.

[3-45] The compound or composition of [3-42] wherein eicosapentaenoic acid ethyl ester or docosahexaenoic acid ethyl ester obtained by purification is contained at a content of equal to or greater than about 80%, equal to or greater than about 85%, equal to or greater than about 86%, equal to or greater than about 90%, equal to or greater than about 95%, equal to or greater than about 96.5%, equal to or greater than about 98%, equal to or greater than about 99%, equal to or greater than about 99.5%, equal to or greater than about 99.8%, or g equal to or greater than about 99.9%.

Some embodiments of the present disclosure are directed to methods of purifying one or more compounds by column chromatography comprising: adding a stationary phase to a column, and allowing a slurry comprising the stationary phase to settle in the column for a settling time.

Some embodiments of the present disclosure are directed to methods of packing a chromatography column comprising: adding a stationary phase to a column, and allowing a slurry comprising the stationary phase to settle in the column for a settling time.

Some embodiments of the present disclosure are directed to methods of increasing theoretical plate number (N) in a column chromatography comprising: adding a stationary phase to a column, and allowing a slurry comprising the stationary phase to settle in the column for a settling time, wherein the increase in N is relative to a column chromatography without settling time or wherein the increase in N is relative to a slurry that settles for a reduced settling time that is less than the settling time.

Some embodiments of the present disclosure are directed to methods of improving symmetry factor of a chromatographic peak in column chromatography comprising allowing a slurry to settle in the column for a settling time, wherein the improvement comprises decreasing the symmetry factor of the peak to a quantity $\geq 1$, and wherein the decrease is relative to a symmetry factor when a column chromatography comprises a reduced settling time that is absent or less than the settling time and the symmetry factor is >1; or the improvement comprises increasing the symmetry factor of the peak to a quantity $\leq 1$, and wherein the increase is relative to a symmetry factor when the column chromatography comprises a reduced settling time that is absent or less than the settling time and the symmetry factor is <1. In some embodiments, all chromatography conditions other than settling time are identical when the column chromatography comprises the settling time and when the column chromatography comprises the reduced settling time that is absent or less than the settling time.

In some embodiments of these methods, the column is under atmospheric pressure during settling time. In some embodiments of these methods, pressure is applied to the column after settling time. In some embodiments of these methods, each settling time is independently between about 0.5 minutes to about 2 minutes, about 2 minutes to about 4 minutes, about 4 minutes to about 6 minutes, about 6 minutes to about 8 minutes, about 8 minutes to about 10 minutes, about 10 minutes to about 12 minutes, about 12 minutes to about 14 minutes, about 14 minutes to about 16 minutes, about 16 minutes to about 18 minutes, about 18 minutes to about 20 minutes, about 20 minutes to about 22 minutes, about 22 minutes to about 24 minutes, about 24 minutes to about 26 minutes, about 26 minutes to about 28 minutes, about 28 minutes to about 30 minutes, about 30 minutes to about 32 minutes, about 32 minutes to about 34 minutes, about 34 minutes to about 36 minutes, about 36 minutes to about 38 minutes, or about 38 minutes to about 40 minutes. In some embodiments, the settling time is independently between about 0.5 minutes to about 5 minutes, about 5 minutes to about 10 minutes, about 10 minutes to about 15 minutes, about 15 minutes to about 20 minutes, about 20 minutes to about 25 minutes, about 25 minutes to about 30 minutes, about 30 minutes to about 35 minutes, about 35 minutes to about 40 minutes, about 40 minutes to about 45 minutes, about 45 minutes to about 50 minutes, about 50 minutes to about 55 minutes, about 55 minutes to about 60 minutes, about 60 minutes to about 65 minutes, about 65 minutes to about 70 minutes, about 70 minutes to about 75 minutes, about 75 minutes to about 80 minutes, about 80 minutes to about 85 minutes, about 85 minutes to about 90 minutes, about 90 minutes to about 95 minutes, or about 95 minutes to about 100 minutes, about 100 minutes to about 105 minutes, about 105 minutes to about 110 minutes, about 110 minutes to about 115 minutes, about 115 minutes to about 120 minutes.

Some embodiments of the present disclosure are directed to methods of purifying one or more compounds by column chromatography comprising decreasing sedimentation volume in a slurry, wherein the decrease in sedimentation volume is relative to the sedimentation volume of a fresh slurry.

Some embodiments of the present disclosure are directed to methods of packing a chromatography column comprising decreasing sedimentation volume in a slurry, wherein the decrease in sedimentation volume is relative to the sedimentation volume of a fresh slurry.

Some embodiments of the present disclosure are directed to methods of increasing theoretical plate number (N) in a column chromatography comprising decreasing sedimentation volume in a slurry, wherein the decrease in sedimentation volume is relative to a sedimentation volume of a fresh slurry, and wherein the increase in Nis relative to an N of a column chromatography wherein the column is packed with the fresh slurry.

Some embodiments of the present disclosure are directed to methods of improving symmetry factor of a chromatographic peak in column chromatography comprising decreasing sedimentation volume in a slurry before column packing, wherein the decrease in sedimentation volume is relative to the sedimentation volume of a fresh slurry, wherein the improvement comprises decreasing the symmetry factor of the peak to a quantity ≥1 if the symmetry factor for the peak >1 when column chromatography is performed with a column packed with fresh slurry; or the improvement comprises increasing the symmetry factor of the peak to a quantity ≤1 if the symmetry factor for the peak <1 when column chromatography is performed with a column packed with fresh slurry.

In some embodiments of these methods, all chromatography conditions other than sedimentation volume are identical when the column chromatography comprises the decreased sedimentation volume and when the column chromatography is performed with a column packed with fresh slurry. In some embodiments of these methods, the fresh slurry comprises a mobile phase (or solvent) and a stationary phase combined for more than about 0.5 minutes, 1 minute, 2 minutes, 5 minutes, 10 minutes, 20 minutes, 30 minutes, 40 minutes, 50 minutes, 60 minutes, 70 minutes, 80 minutes, 90 minutes, 100 minutes, 110 minutes, 120 minutes and/or less than 200 minutes, 185 minutes, 175 minutes, 165 minutes, 155 minutes, 145 minutes, 135 minutes, 125 minutes, 115 minutes, 105 minutes, 95 minutes, 85 minutes, 75 minutes, 65 minutes, 55 minutes, 45 minutes, 35 minutes, 25 minutes. Combining the mobile phase (or solvent) and the stationary phase includes agitation. In some embodiments of these methods, the decrease in sedimentation volume is over an amount of time between about 0 minutes to about 2 minutes, about 2 minutes to about 4 minutes, about 4 minutes to about 8 minutes, about 8 minutes to about 16 minutes, about 16 minutes to about 24 minutes, about 24 minutes to about 32 minutes, about 32 minutes to about 50 minutes, about 50 minutes to about 70 minutes, about 70 minutes to about 90 minutes, about 90 minutes to about 110 minutes, about 110 minutes to about 130 minutes, about 130 minutes to about 150 minutes. In some embodiments of these methods, the sedimentation volume remains substantially constant after the amount of time. In some embodiments of these methods, the decrease in sedimentation volume is over a settling time. In some embodiments of these methods, wherein decreasing sedimentation volume comprises allowing the mixture to settle at atmospheric pressure. In some embodiments of these methods, pressure is applied to the column after the decrease in sedimentation volume. In some embodiments of these methods, the column is an axial compression column. In some embodiments of these methods, the slurry comprises a stationary phase and one or more of water, methanol, ethanol, acetonitrile, ethyl acetate, hexanes, or dichloromethane. In some embodiments of these methods, the slurry comprises methanol. In some embodiments of these methods, the stationary phase comprises particles of C30, C22, C18, C8, C5, C4, biphenyl, fluorophenyl, hydrophilic interaction liquid chromatography (HILIC) stationary phase, acrylamide, silica, phenyl-hexyl stationary phase, polar embedded alkyl, and/or fluorophenyl propyl. In some embodiments of these methods, the stationary phase is particles of C18.

The method of any one of the above embodiments, wherein chromatography comprises elution with a mobile phase comprising one or more of water, methanol, ethanol, acetonitrile, ethyl acetate, hexanes, dichloromethane, or supercritical carbon dioxide. In some embodiments of these methods, the mobile phase comprises methanol. In some embodiments of these methods, chromatography comprises a mobile phase comprising an additive selected from one or more of formic acid, ammonium formate, trimethylamine, ammonia, and ammonium hydroxide. In some embodiments of these methods, column chromatography comprises a mobile phase gradient. In some embodiments of these methods, chromatography comprises the purification of one or more analytes selected from fatty acids or esterified derivatives thereof, proteins, nucleic acids, and small molecules. In some embodiments of these methods, chromatography comprises the purification of one or more fatty acids or an esterified derivative thereof. In some embodiments of these methods, the fatty acids are selected from one or more of docosahexaenoic acid, crotonic acid, myristoleic acid, palmitoleic acid, sapienic acid, oleic acid, elaidic acid, vaccenic acid, gadoleic acid, eicosenoic acid, erucic acid, nervonic acid, linoleic acid, eicosadienoic acid, docosadienoic acid, linolenic acid, pinolenic acid, eleostearic acid, mead acid, dihomo-γ-linolenic acid, eicosatrienoic acid, stearidonic acid, arachidonic acid, eicosatetraenoic acid, adrenic acid, bosseopentaenoic acid, eicosapentaenoic acid, ozubondo acid, sardine acid, tetracosanolpentaenoic acid, cervonic acid, herring acid, propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, carboceric acid, montanic acid, nonacosylic acid, melissic acid, hentriacontylic acid, lacceroic acid, psyllic acid, geddic acid, ceroplastic acid, hexatriacontylic acid, heptatriacontylic acid, octatriacontylic acid, nonatriacontylic acid, and tetracontylic acid. In some embodiments of these methods, the esterified derivative thereof is a methyl, ethyl, propyl, butyl, pentyl, hexyl, heptyl, octyl, nonyl, or decyl ester. In some embodiments of these methods, n chromatography comprises the purification of eicosapentaenoic acid ethyl ester. In some embodiments of these methods, the slurry is formed by: a) premixing a stationary phase and a mobile phase (or solvent) prior to addition of slurry to the column; or b) adding mobile phase (or solvent) to the column then adding stationary phase to the mobile phase. In some embodiments of these methods, the stationary phase is added to the mobile phase (or solvent) portion wise.

Other embodiments include a compound or composition comprising the compound purified by the methods of this disclosure. In some embodiments, the compound is a fatty acid or esterified derivative thereof, protein, nucleic acid, or small molecule. In some embodiments, the compound is a fatty acid or an esterified derivative thereof. In some embodiments, the compound is docosahexaenoic acid, crotonic acid, myristoleic acid, palmitoleic acid, sapienic acid, oleic acid, elaidic acid, vaccenic acid, gadoleic acid, eicosenoic acid, erucic acid, nervonic acid, linoleic acid, eicosadienoic acid, docosadienoic acid, linolenic acid, pinolenic acid, eleostearic acid, mead acid, dihomo-γ-linolenic acid, eicosatrienoic acid, stearidonic acid, arachidonic acid, eicosatetraenoic acid, adrenic acid, bosseopentaenoic acid, eicosapentaenoic acid, ozubondo acid, sardine acid, tetracosanolpentaenoic acid, cervonic acid, herring acid, propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, carboceric acid, montanic acid, nonacosylic acid, melissic acid, hentriacontylic acid, lacceroic acid, psyllic acid, geddic acid, ceroplastic acid, hexatriacontylic acid, heptatriacontylic acid, octatriacontylic acid, nonatriacontylic acid, tetracontylic acid, or an esterified derivative thereof. In some embodiments, the esterified derivative thereof is a methyl, ethyl, propyl, butyl, pentyl, hexyl, heptyl, octyl, nonyl, or decyl ester. In some embodiments, the compound or composition is eicosapentaenoic acid ethyl ester. In some embodiments, the compound or composition comprising a purity of greater than about 50%, greater than about 60%, greater than about 70%, greater than about 80%, greater than about 85%, greater than about 86%, greater than about 90%, greater than about 95%, greater than about 96.5%, greater than about 98%, greater than about 99%, greater than about 99.5%, greater than about 99.8%, or greater than about 99.9% and/or less than about 99.95%, less than about 99.99%. In some embodiments, the yield is greater than 50%, greater than 55%, greater than 60%, greater than 65%, greater than 70%, greater than 75%, greater than 80%, and/or less than 75%, less than 80%, less than 85%, less than 90%, or less than 95%. In some embodiments, the recovery rate is greater than 55%, greater than 60%, greater than 65%, greater than 70%, greater than 75%, greater than 80%, greater than 85%, greater than 90%, greater than 95%, greater than 98%, greater than 99%, or greater than 99.7%, and/or less than 95%, less than 97%, less than 98%, less than 99%, less than 99.5%, less than 99.7% or less than 99.9%.

DESCRIPTION OF EMBODIMENTS

Figure 1:
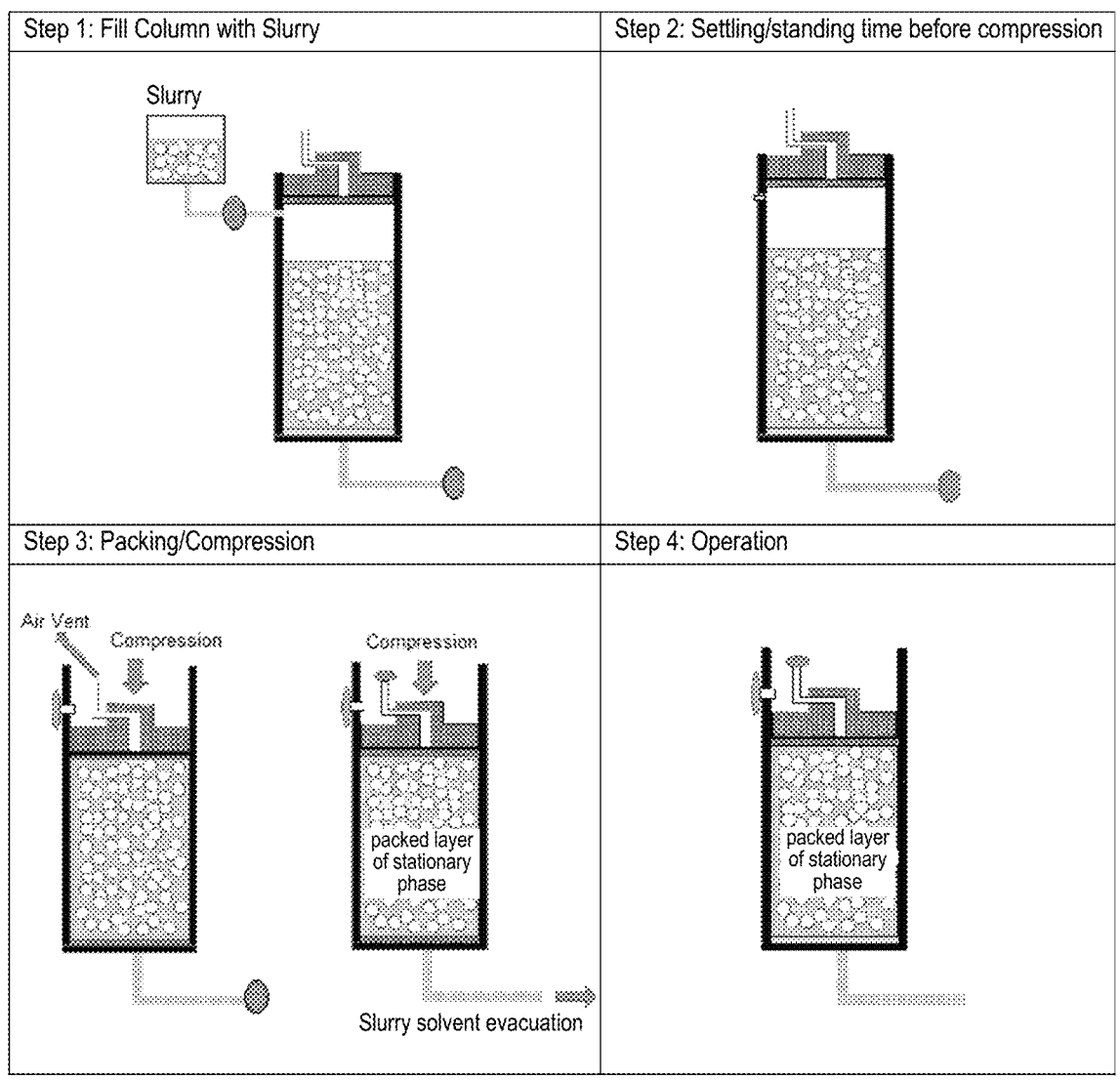
FIG. 1 shows a step-wise schematic of the settling and packing process of an embodiment of this disclosure. The packed layer of stationary phase is a slurry support.

A fatty acid is a carboxylic acid with a long aliphatic chain, which is either saturated or unsaturated. Fatty acids are usually produced industrially by the hydrolysis of triglycerides or phospholipids derived from natural sources. Some are produced synthetically. Regardless of the method of production, purification methods are required to obtain pure product for food, cosmetic, or industrial use.

The present disclosure is directed to the discovery that purification of eicosapentaenoic acid ethyl ester (EPA-E) and/or docosahexaenoic acid ethyl ester (DHA-E) by column chromatography can be improved by allowing a slurry of a stationary phase and a mobile phase (or solvent) an extended settling time after addition to the column which facilitates reduced sedimentation volume of the slurry before packing the column. This results in improved column performance versus packing the column immediately upon introduction of the slurry to the column. Improvements in column performance include increased theoretical plate number and more symmetrical peaks.

Thus in one aspect a method of purifying one or more compounds by chromatography is provided comprising allowing a slurry to settle in a column for a period of time. In another aspect, a method of packing a chromatography column is provided comprising allowing a slurry to settle in the column for a period of time Columns are cylindrical having an outer diameter, inner diameter, and length. In some embodiments, the column is a preparative chromatography column. Preparative chromatography columns may comprise in inner diameter of about 10 mm to about 2 m and a length between about 100 mm to about 5 m, between about 2 cm to about 2 m, or between about 5 cm to about 80 cm. In some embodiments the column is an analytical chromatography column. Analytical columns may comprise an inner diameter of about 1 mm to about 10 cm and a length of about 10 mm to about 500 mm. The dimensions may be selected so that the inner diameter is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 120%, about 140%, about 160%, about 180%, about 200%, about 220%, about 240%, about 260%, about 280%, about 300%, about 320%, about 340%, about 360%, about 380%, about 400%, about 450% or about 500% of the length. The outer diameter may be about 0.1%, about 0.5%, about 1.0%, about 1.5%, about 2.0%, about 2.5%, about 3.0%, about 3.5%, about 4.0%, about 4.5%, about 5%, about 7.5%, about 10%, about 15%, about 20%, about 25%, or about 30% greater than the inner diameter.

The slurry may comprise of a stationary phase and a mobile phase (or solvent). The stationary phase may be selected from C30, C22, C18, C8, C5, C4, biphenyl, fluorophenyl, hydrophilic interaction liquid chromatography (HILIC) stationary phase, acrylamide, silica, phenyl-hexyl stationary phase, polar embedded alkyl, fluorophenyl propyl or any stationary phase known in the art of chromatography. In some embodiments, a chiral stationary phase is used. Selection of stationary phase will be apparent to those of ordinary skill in the art and may depend on the analyte to be purified by chromatography. Nonpolar analytes such as fatty acids or fatty acid esters (e.g., EPA-E and/or DHA-E) may require use of a reverse phase stationary phase, for example, C18 (ODS). Different varieties of octadecyl-silica (ODS) may be used including fully end-capped, partially end-capped, and base deactivated. More polar analytes may require regular phase stationary phases such as non-bonded silica, amino phase, or cyano phase.

The slurry concentration (slurry concentration (%)=stationary phase (g)/solvent (ml)×100) may be between about 20% to about 30%, about 30% to about 40%, about 40% to about 50%, about 50% to about 60%, or about 60% to about 70%. In one embodiment, the slurry concentration is about 20% to about 70%, preferably about 30% to about 70%, more preferably about 30% to about 60%.

In some embodiments, the stationary phase comprises particles having a median particle diameter between about 1 µm to about 20 µm, about 20 µm to about 40 µm, about 40 µm to about 60 µm, about 60 µm to about 80 µm, about 80 µm to about 1000 µm, about 1000 µm to about 2000 µm, about 2000 µm to about 3000 µm, about 3000 µm to about 4000 µm, about 4000 µm to about 5000 µm. In some embodiments, the stationary phase comprises particles having a median particle diameter of greater than 50 µm, greater than 45 µm, greater than 40 µm, greater than 35 µm, greater than 30 µm, greater than 25 µm, greater than 20 µm, greater than 15 µm, or greater than 10 µm and/or less than 500 µm, less than 400 µm, less than 300 µm, less than 200 µm, less than 100 µm, less than 80 µm, less than 60 µm. The median particle diameter may be measured by laser diffraction scattering method, as understood by one of skill in the art.

Mobile phases may include one or more of water, methanol, ethanol, acetonitrile, ethyl acetate, hexanes, dichloromethane, supercritical carbon dioxide or any other solvent known in the art. Selection of mobile phases may require consideration of the analyte to be purified and the stationary phase used. In reverse phase stationary phases with nonpolar analytes, selection of a polar mobile phase sufficient to elute the compound of interest, but not cause elution so soon as to be near the solvent front should be selected.

Mobile phases may further comprises additives including buffering agents and pH adjusters. Selection of additives may be determined based on mobile phases used, stationary phases used, and analytes to be purified. In some embodiments, a mobile phase comprises an additive selected from one or more of formic acid, ammonium formate, trimethylamine, ammonia, and ammonium hydroxide. In some embodiments, the mobile phase may be free of an additive.

In some embodiments, a solvent gradient may be used for the mobile phase during elution. The main purpose of gradient elution is to elute analytes that are strongly retained by the column faster, while having the weakly retained analytes eluted more slowly so that eluted analytes produce well resolved peaks upon detection. For example, in reversed phase chromatography, starting with a low content of the nonpolar solvent in the eluent allows the weakly retained analytes to be separated. Strongly retained analytes will remain on the adsorbent surface at the top of the column, or will move very slowly. Increasing the amount of nonpolar component in the eluent (e.g., acetonitrile) allows strongly retained components to move faster, because of the steady increase of the competition for the adsorption sites by the nonpolar solvent.

Thus, in reverse phase chromatography with nonpolar analytes the solvent and the beginning of elution in chromatography may include a high percentage of a polar Solvent A, for example, water, selected from about 100%, about 90%, about 80%, about 70%, about 60%, about 50%, about 40%, about 30%, about 20%, about 10%, or about 0%. Solvent B may be solvent more nonpolar than Solvent A, for example methanol (in the case were Solvent A is water). Solvent B will make up the remaining percentage of the mobile phase. As the column is run and solvent is eluted through the stationary phase and the column, the gradient will result in a gradual increase in the concentration of Solvent B over time. In some embodiments, a solvent consisting of a single composition may be used as the mobile phase. In some embodiments, one or more of water, methanol, ethanol, acetonitrile, ethyl acetate, hexanes, dichloromethane, supercritical carbon dioxide or any other solvent known in the art may be used alone or in combination as the solvent consisting of a single composition.

In embodiments using normal phase stationary phase and/or polar analytes, the mobile phase comprises a percentage of Solvent A of about 100%, about 90%, about 80%, about 70%, about 60%, or about 50%, wherein solvent A is a nonpolar solvent, for example, hexanes. Solvent B will make the remaining percentage of the mobile phase and may comprise polar solvent, for example, ethyl acetate, diethyl ether, dichloromethane, or tert-butyl dimethyl ether. The percentage of Solvent B will increase over time during elution with the gradient.

In some embodiments the rate of B increase over time may be constant. In some embodiments there is no gradient and the mobile phase is isocratic during elution. In some embodiments, different rates of increase of Solvent B percentage at different time ranges within the chromatography method may be employed. In some embodiments, certain time ranges of the chromatography method may be isocratic and others involve a gradient.

Solvents used in the mobile phase may be stored separately in a mobile phase supply and mixed using a pump prior to elution through the column. A mobile phase supply comprises a mobile phase source and a solvent delivery system. Such a solvent delivery system is a pumping device such as commercially available HPLC pumps, which provide solvent or mobile phase to a column. Such pumps generally provide pulse-free flows, flow rates ranging from 0.1-100 L/min, accurate control of flow rate, generation of high pressure (up to 6000 psi), and corrosion- and solvent-resistant components. Reciprocating pumps consist of a small chamber into which the solvent is pumped by the back and forth motion of a motor-driven piston. Two check valves, which open and close alternately, control the direction and flow of solvent in and out of a cylinder. Single-piston pumps use specially designed cams to permit very rapid refill times, producing a more continuous flow. The disadvantage of pulsed flows with reciprocating pumps is often overcome by using a pulse damper. The use of a dual-piston pump, which operates with the pistons moving out of phase with each other, offers a reasonable solution for pulse-free fluid delivery. The linear velocity of a column is the velocity of the fluid passing through a cross sectional area of the column. The linear velocity (linear velocity (m/hr)=flow rate (m$^3$/hr)/column cross sectional area (m$^2$)) may be about 0.2 to 1.0 m/hr, about 1.0 to 3.0 m/hr, about 3.0 to 6.0 m/hr, about 6.0 to 10.0 m/hr or about 10.0 to 20.0 m/hr. In one embodiment, the linear velocity is about 4.0 to 9.0 m/hr.

Mobile phase gradients may be generated through high pressure mixing, which requires a pump for each solvent, or low pressure mixing which requires only one pump. In high-pressure mixing systems, individual high pressure pumps are used to provide each solvent. The outlet of each pump is either connected to a mixing connector (usually referred to as a "T" since there are normally two inlet lines and one outlet line) or to a mixing chamber. Thus, the two solvents are blended en route to the column, that is, mixing is accomplished on the high-pressure side of the pumps. The generation of a mobile phase gradient created from three solvents may be accomplished by utilizing three separate pumps. In low-pressure systems, mixing is accomplished prior to the pump, at its low-pressure side and the overall flow rate is controlled by a single pump. Proportioning valves, normally solenoid operated, are used to deliver the individual solvents. The controller simply divides the signal according to the percentage of each component and each valve is opened for the proper period of time. Usually the valves deliver the individual solvents into a mixing chamber which then feeds the blended solvent to the pump. In some systems, the valves feed the mobile phase components through a mixing connector directly to the high-pressure pump. Programmable flow rate control is desirable for gradient generation by either method.

The settling during the settling time preferable occurs at atmospheric pressure (about 0.101325 MPa). In some embodiments, the pressure during settling time is between about 0.1 MPa to about 0.2 MPa, about 0.2 MPa to about 0.4 MPa, about 0.4 MPa to about 0.6 MPa, about 0.6 MPa to about 0.8 MPa, or about 0.8 MPa to about 1 MPa. In some embodiments, the pressure during settling time is less than about 0.1 MPa. In some embodiments, the pressure during settling time is atmosphere pressure. In some embodiments, the pressure during settling time is greater than 0.01 MPa, greater than 0.05 MPa, or greater than 0.1 MPa and/or less than 1 MPa, less than 0.8 MPa, less than 0.6 MPa, less than 0.4 MPa or less than 0.2 MPa.

In some embodiments, a detector is used to monitor mobile phase eluting from the column for presence of analyte(s). Detection methods known in the art may be used, for example, mass spectrometry (MS), UV/Vis absorbance, fluorescence, refractive index, or conductivity.

MS relates to methods of filtering, detecting, and measuring ions based on their massto-charge ratio, or "m/z." In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. Nos. 6,204,500, entitled "Mass Spectrometry From Surfaces;" 6,107,623, entitled "Methods and Apparatus for Tandem Mass Spectrometry;" 6,268,144, entitled "DNA Diagnostics Based On Mass Spectrometry;" 6,124, 137, entitled "Surface-Enhanced Photolabile Attachment And Release For Desorption And Detection Of Analytes;" Wright et al., *Prostate Cancer and Prostatic Diseases* 2:264-76 (1999); and Merchant and Weinberger, *Electrophoresis* 21:1164-67 (2000), each of which is hereby incorporated by reference in its entirety, including all tables, figures, and claims.

For example, in a "quadrupole" or "quadrupole ion trap" instrument, ions in an oscillating radio frequency field experience a force proportional to the DC potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

Moreover, one can often enhance the resolution of the MS technique by employing "tandem mass spectrometry," or "MS/MS." In this technique, a first, or parent, ion generated from a molecule of interest can be filtered in an MS instrument, and these parent ions subsequently fragmented to yield one or more second, or daughter, ions that are then analyzed in a second MS procedure. By careful selection of parent ions, only ions produced by certain analytes are passed to the fragmentation chamber, where collision with atoms of an inert gas to produce these daughter ions. Because both the parent and daughter ions are produced in a reproducible fashion under a given set of ionization/fragmentation conditions, the MS/MS technique can provide an extremely powerful detection tool. For example, the combination of filtration/fragmentation can be used to eliminate interfering substances, and can be particularly useful in complex samples, such as biological samples.

Additionally, recent advances in technology, such as matrix-assisted laser desorption ionization coupled with time-of-flight analyzers ("MALDI-TOF") permit the analysis of analytes at femtomole levels in very short ion pulses. Mass spectrometers that combine time-of-flight analyzers with tandem MS are also well known to the artisan. Additionally, multiple mass spectrometry steps can be combined in methods known as "MS/MSn." Various other combinations may be employed, such as MS/MS/TOF, MALDI/MS/MS/TOF, or SELDI/MS/MS/TOF mass spectrometry.

Ions can be produced using a variety of methods including, but not limited to, electron ionization, chemical ionization, fast atom bombardment, field desorption, and matrix-assisted laser desorption ionization ("MALDI"), surface enhanced laser desorption ionization ("SELDI"), photon ionization, electrospray ionization, and inductively coupled plasma.

The term "electron ionization" as used herein refers to methods in which an analyte of interest in a gaseous or vapor phase is interacted with a flow of electrons. Impact of the electrons with the analyte produces analyte ions, which may then be subjected to a mass spectroscopy technique.

The term "chemical ionization" as used herein refers to methods in which a reagent gas (e.g. ammonia) is subjected to electron impact, and analyte ions are formed by the interaction of reagent gas ions and analyte molecules.

The term "fast atom bombardment" as used herein refers to methods in which a beam of high energy atoms (often Xe or Ar) impacts a non-volatile test sample, desorbing and ionizing molecules contained in the sample. Samples are dissolved in a viscous liquid matrix, such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

The term "field desorption" as used herein refers to methods in which a non-volatile test sample is placed on an ionization surface, and an intense electric field is used to generate analyte ions.

The term "matrix-assisted laser desorption ionization," or "MALDI" as used herein refers to methods in which a non-volatile sample is exposed to laser irradiation, which desorbs and ionizes analytes in the sample by various ionization pathways, including photoionization, protonation, deprotonation, and cluster decay. For MALDI, the sample is mixed with an energyabsorbing matrix, which facilitates desorption of analyte molecules.

The term "surface enhanced laser desorption ionization," or "SELDI" as used herein refers to another method in which a non-volatile sample is exposed to laser irradiation, which desorbs and ionizes analytes in the sample by various ionization pathways, including photoionization, protonation, deprotonation, and cluster decay. For SELDI, the sample is typically bound to a surface that preferentially retains one or more analytes of interest. As in MALDI, this process may also employ an energy-absorbing material to facilitate ionization.

The term "electrospray ionization" or ESI as used herein refers to methods in which a solution is passed along a short length of capillary tube, to the end of which is applied a high positive or negative electric potential. Solution reaching the end of the tube, is vaporized (nebulized) into a jet or spray of very small droplets of solution in solvent vapor. This mist of droplets flows through an evaporation chamber which is heated slightly to prevent condensation and to evaporate solvent. As the droplets get smaller the electrical surface charge density increases until such time that the natural repulsion between like charges causes ions as well as neutral molecules to be released.

The term "Atmospheric Pressure Chemical Ionization," or "APCI," as used herein refers to methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated N2 gas may be used to improve removal of solvent. The gasphase ionization in APCI can be more effective than ESI for analyzing less-polar species.

The term "inductively coupled plasma" as used herein refers to methods in which a sample is interacted with a partially ionized gas at a sufficiently high temperature to atomize and ionize most elements.

The term "ionization" as used herein refers to the process of generating an analyte ion having a net electrical charge equal to one or more electron units. Negative ions are those ions having a net negative charge of one or more electron units, while positive ions are those ions having a net positive charge of one or more electron units.

The term "operating in negative ion mode" refers to those mass spectrometry methods where negative ions are detected. Similarly, "operating in positive ion mode" refers to those mass spectrometry methods where positive ions are detected.

The term "desorption" as used herein refers to the removal of an analyte from a surface and/or the entry of an analyte into a gaseous phase.

In those embodiments, such as MS/MS, where parent ions are isolated for further fragmentation, collision-induced dissociation, or "CID," is often used to generate the ion fragments for further detection. In CID, parent ions gain energy through collisions with an inert gas, and subsequently fragment by a process referred to as "unimolecular decomposition." Sufficient energy must be deposited in the parent ion so that certain bonds within the ion can be broken due to increased vibrational energy.

In other embodiments, any of a variety of standard HPLC detectors can be used for the detection of the analyte upon elution from the analytical column. In this case, the elution of a compound from the column is detected as a peak in a chromatogram. The retention time of the peak is used to identify the compound, and the peak height (or area) is proportional to the amount of the compound in the sample. The "retention time" is the time required for an analyte to pass through a chromatographic system and is measured from the time of injection of sample (or loading of sample) to the time of detection. Ideally, each analyte of interest will have a characteristic retention time. However, the retention of an analyte often differs considerably between experiments and laboratories due to variations of the eluent, the stationary phase, temperature, and the setup of the chromatographic system. Therefore the retention time of the test analyte is compared to that of one or more standard compounds under identical conditions. An appropriate detector exhibits good sensitivity, good stability, reproducibility, linear response if used for quantitative purposes, over a few orders of magnitude, short response time, and ease of operation. Such detectors include, but are not limited to, UV/Vis absorbance detectors, photodiode array detectors, fluorescence detectors, refractive index detectors, and conductivity detectors.

UV/Vis absorbance detectors consisting of a scanning spectrophotometer with grating optics can be used. The independent or combined use of a Deuterium source (UV range, 190-360 nm) with a Tungsten source (visible range, 360-800 nm) provides a simple means of detecting absorbing species as they emerge from the column.

Photodiode-array (PDA)-based instruments are UV/Vis absorbance detectors that permit very rapid collection of data over a selected spectral range. Absorbance spectral data for each chromatographic peak can be collected and stored. Stored data may be compared with the spectrum of a pure standard from a library. The PDA detector is useful in the identification of components that are difficult to resolve (overlapping peaks) since the characteristic spectrum for each of the unresolved components is likely to be different.

Fluorescence detectors are useful in the detection of analytes that exhibit a chemiluminescent property such as fluorescence or phosphorescence. They are more sensitive than UV absorbance detectors by at least one order of magnitude. Fluorescence is typically observed by detection of the grating-isolated emission radiation at a 90-degree angle to the excitation beam. The number of fluorescing species can be enhanced by a post-column derivatization (PCD) reaction of the eluted compounds (or pre-column derivatization reaction of the sample itself) with special reagents.

Refractive index (RI) detectors respond to nearly all solutes. The difference in the refractive index of the reference mobile phase versus the column effluent results in the detection of separated components as peaks on the chromatogram. Because of its extreme sensitivity to the mobile phase, this detector may not be used without adequate pulse-damping within the LC pump, nor is it suitable for gradient applications because of the changing mobile phase composition. The detection limits are usually lower than those observed with absorbance detectors.

Conductivity detectors provide high-sensitivity detection of all charged species. This detector may be used with an LC system for the simple and reliable detection of anions, cations, metals, organic acids, and surfactants down to the ppb level. The addition of a chemical suppressor between the column and conductivity detector serves to reduce the eluant conductivity, allowing the use of gradient elution and the determination of ppb levels with minimum baseline drift. For a typical determination of low levels of anions, the eluant is converted to its weakly ionized low-conductivity acid (e.g., Na2CO3 to carbonic acid), reducing the background noise. At the same time, the analyte anions are converted to their corresponding high-conductivity acids (e.g., NaCl to HCl), increasing the relative analyte signal.

In another aspect, a method of increasing theoretical plate number (N) in a column chromatography is provided comprising decreasing sedimentation volume in a slurry, wherein the decrease in sedimentation volume is relative to a sedimentation volume of a fresh slurry, and wherein the increase in N is relative to an N of a column chromatography wherein the column is packed with the fresh slurry.

In another aspect, a method of increasing theoretical plate number (N) in a column chromatography is provided comprising allowing a slurry to settle in the column for a settling time, wherein the increase is relative to a column chromatography without settling time or wherein slurry settles for a reduced settling time that is less than the settling time.

In some embodiments, the increased N is between about 1,000 to about 1,500, about 1,5000 to about 2,000, about 2,000 to about 2,500, about 2,500 to about 3,000, about 3,000 to about 4,000, about 4,000 to about 5,000, about 5,000 to about 6,000, about 6,000 to about 8,000, about 8,000 to about 11,000, or about 11,000 to about 15,000. In some embodiments, the increased N is greater than about 500, greater than about 1,000, greater than about 1,500 or greater than about 2,000 and/or less than about 20,000, less than about 15,000, or less than about 10,000. The increase in N may be an increase of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% or greater.

In another aspect, a method of improving symmetry factor(S) of a chromatographic peak in column chromatography is provided comprising allowing a slurry to settle in the column for a settling time, wherein the improvement comprises decreasing the symmetry factor of the peak to a quantity ≥1, and wherein the decrease is relative to a symmetry factor when a column chromatography comprises a reduced settling time that is absent or less than the settling time and the symmetry factor is >1; or the improvement comprises increasing the symmetry factor of the peak to a quantity ≤1, and wherein the increase is relative to a symmetry factor when a column chromatography comprises a reduced settling time that is absent or less than the settling time and the symmetry factor is <1.

In another aspect, a method of improving symmetry factor(S) of a chromatographic peak in column chromatography is provided comprising decreasing sedimentation volume in a slurry before column packing, wherein the decrease in sedimentation volume is relative to a sedimentation volume of a fresh slurry, wherein the improvement comprises decreasing the symmetry factor of the peak to a quantity ≥1 if the symmetry factor for the peak >1 when column chromatography is performed with a column packed with fresh slurry; or the improvement comprises increasing the symmetry factor of the peak to a quantity ≤1 if the symmetry factor for the peak <1 when column chromatography is performed with a column packed with fresh slurry.

In some embodiments, the increase or decrease in S may be an increase or decrease of about 3%, about 5%, about 10%, about 15%, about 20%, about 25%, about 30%, about 35%, about 40%, about 45%, about 50%, about 55%, about 60%, about 65%, about 70%, about 75%, or about 80%. In some embodiments, the increase or decrease in S may be an increase or decrease of greater than about 1%, greater than about 2%, greater than about 3%, greater than 5% or greater than 10% and/or less than about 90%, less than about 80%, less than about 70%, less than about 60%, less than about 50% or less than about 40%.

In another aspect, a method of purifying one or more compounds by chromatography is provided comprising decreasing sedimentation volume in a slurry, wherein the decrease in sedimentation volume is relative to the sedimentation volume of a fresh slurry.

In another aspect, a method of packing a chromatography column is provided comprising decreasing sedimentation volume in a slurry, wherein the decrease in sedimentation volume is relative to the sedimentation volume of a fresh slurry.

In some embodiments, the sedimentation volume ratio (sedimentation volume ratio (%)=sedimentation volume (ml)/ODS volume (ml)×100) is substantially constant at the completion of settling time. The sedimentation volume ratio may decrease upon addition of slurry to the column until reaching a constant value at completion of the settling time. In some embodiments the sedimentation volume ratio decreases to between about 150% to about 140%, about 140% to about 130%, about 120% to about 110%, or about 110% to about 100%. In some embodiments the sedimentation volume ratio decreases to less than about 160%, less than about 150%, less than about 140% or less than about 130% and/or more than about 100% or more than about 105%.

In some embodiments, the settling time results in improvement of performance, e.g., increased N, S approaching 1, increased yield or recovery rate, and/or decreased sedimentation volume, and is between about 15 and about 25 minutes, about 18 and about 22 minutes, or is about 20 minutes. In some embodiments, each settling time is independently between about 0.5 minutes to about 5 minutes, about 5 minutes to about 10 minutes, about 10 minutes to about 15 minutes, about 15 minutes to about 20 minutes, about 20 minutes to about 25 minutes, about 25 minutes to about 30 minutes, about 30 minutes to about 35 minutes, about 35 minutes to about 40 minutes, about 40 minutes to about 45 minutes, about 45 minutes to about 50 minutes, about 50 minutes to about 55 minutes, about 55 minutes to about 60 minutes, about 60 minutes to about 65 minutes, about 65 minutes to about 70 minutes, about 70 minutes to about 75 minutes, about 75 minutes to about 80 minutes, about 80 minutes to about 85 minutes, about 85 minutes to about 90 minutes, about 90 minutes to about 95 minutes, or about 95 minutes to about 100 minutes, about 100 minutes to about 105 minutes, about 105 minutes to about 110 minutes, about 110 minutes to about 115 minutes, about 115 minutes to about 120 minutes. In some embodiments, each settling time is independently more than about 0.5 minutes, 1 minute, 2 minutes, 5 minutes, 10 minutes, 20 minutes, 30 minutes, 40 minutes, 50 minutes, 60 minutes, 70 minutes, 80 minutes, 90 minutes, 100 minutes, 110 minutes, 120 minutes, 130 minutes, 140 minutes, 150 minutes, 200 minutes, 300 minutes, 400 minutes, 500 minutes, 600 minutes, 1200 minutes, 1440 minutes, 2880 minutes and/or less than 200 minutes, 185 minutes, 175 minutes, 165 minutes, 155 minutes, 145 minutes, 135 minutes, 125 minutes, 115 minutes, 105 minutes, 95 minutes, 85 minutes, 75 minutes, 65 minutes, 55 minutes, 45 minutes, 35 minutes, 25 minutes, 15 minutes, 5 minutes, 3 minutes. Longer settling time may provide better symmetry factor and/or theoretical plate number while shorter setting time may provide increased ease of preparation of the column, which may result in increased productivity. One may choose suitable settling time for desired purpose.

A slurry is prepared by mixing of solvent or mobile phase with stationary phase. Slurry may be prepared externally to the column then pumped into the column or slurry may be prepared within the column by addition of solvent to the column followed by addition of dry stationary phase to the solvent in the column. The addition may be the total volume at once or portion wise in several times. Alternatively, dry stationary phase may be added to a dry column followed by addition of solvent to the column to form the slurry. A fresh slurry comprises solvent or mobile phase and stationary phase combined for less than about 10 minutes, less than about 8 minutes, less than about 6 minutes, less than about 4 minutes, less than about 2 minutes, or less than about 1 minute.

A fresh slurry will have a sedimentation volume ratio higher than the sedimentation volume ratio of the slurry at completion (or during progression of settling) of settling time. In some embodiments, the sedimentation volume ratio of fresh slurry may be decrease to between about 200% to about 180%, about 180% to about 160%, about 160% to about 140%, about 140% to about 130%, about 130% to about 120%, or about 120% to about 110%. In some embodiments, the sedimentation volume ration of fresh slurry may be decrease greater than about 100%, greater than about 110%, greater than about 120% or greater than about 130% and/or less than about 200%, less than about 180%, or less than about 160%.

The method may further comprise packing the column. Packing is preferably performed at the completion of settling time and/or when sedimentation volume decreases and remains substantially constant. Packing may comprise applying a packing pressure to the settled slurry and compressing the slurry within the column. In one embodiment, the packing pressure is a value that includes the atmospheric pressure. The packing pressure may be between about 0.1 MPa to about 0.5 MPa, about 0.5 MPa to about 1 MPa, about 1 MPa to about 1.5 MPa, about 1.5 MPa to about 2 MPa, about 2 MPa to about 2.5 MPa, about 3 MPa to about 3.5 MPa, about 3.5 MPa to about 4 MPa, about 4 MPa to about 4.5 MPa, about 4.5 MPa to about 5 MPa, about 5 MPa to about 5.5 MPa, about 5.5 MPa to about 6 MPa, about 6 MPa to about 6.5 MPa, about 6.5 MPa to about 7 MPa, about 7 MPa to about 7.5 MPa, about 7.5 MPa to about 8 MPa, about 8 MPa to about 8.5 MPa, about 8.5 MPa to about 9 MPa, or about greater than about 9 MPa. In some embodiments, the packing pressure is about 3.0 MPa to about 6.0 MPa. In some embodiments, the packing pressure is greater than about 0.1 MPa, greater than about 0.5 MPa, greater than about 1 MPa, greater than about 2 MPa or greater than about 3 MPa and/or less than about 10 MPa, less than about 9 MPa, less than about 8 MPa, less than about 7 MPa or less than about 6 MPa. The slurry may be compressed during packing and the column vented.

In some embodiments, the method further comprises loading the column with analyte. The column may be flushed with mobile phase of solvent after packing and before loading. After loading, the method may further comprise elution, and fractionation. Detection of analyte as described herein may be performed before, after, or during fractionation. Sample mixtures comprising analyte to be purified may be loaded in a quantity based on the size of the column or mass of stationary phase being used. In some embodiments, a sample mixture may be from about 1 mg to about 10 mg, about 10 mg to about 100 mg, about 100 mg to about 5 g, about 5 g to about 10 g, about 10 g to about 50 g, about 50 g to about 100 g, about 100 g to about 1 kg, about 1 kg to about 10 kg. In some embodiments, a sample mixture may be greater than about 0.5 mg, about 1 mg, about 10 mg, about 100 mg, about 500 mg or about 1 g and/or less than about 20 kg, about 10 kg, or about 5 kg. In some embodiments, the load rate may be from 0.001% to 1.0%, from 0.001% to 5.0%, from 0.01% to 5.0%, from 0.001% to 0.01%, from 0.01% to 0.1%, from 0.1% to 1.0%, from 1.0% to 5.0%.

Fractions of eluted mobile phase containing analyte, sample mixture components, and/or mobile phase may be collected at various time points throughout elution. For example, a new fraction may be collected about every 5 seconds, about every 10 seconds, about every 15 seconds, about every 20 seconds, about every 25 seconds, about every 30 seconds, about every 35 seconds, about every 40 seconds or combinations thereof. In some embodiments, the final fraction may be collected for an extended period of time, for example about 0.5 minute to about 5 minutes, about 5 minutes to about 10 minutes, about 10 minutes to about 20 minutes, about 20 minutes to about 40 minutes. In some embodiments, the final fraction may be collected from an extended period of time longer than about 0.1 minutes, longer than about 0.3 minutes, longer than about 0.5 minutes or longer than 1 minute and/or shorter than 40 minutes, shorter than 30 minutes, shorter than 20 minutes or shorter than 10 minutes.

Analytes to be purified by methods of the disclosure include fatty acids, proteins, nucleic acids, and small molecules such as pharmaceutical compounds or synthetic, or semisynthetic intermediates. Target analytes may be purified from a mixture containing other undesired components such as synthetic byproducts, biological material or matrices, or substances of close structural relation to the target analyte such as positional isomers, stereoisomers, homologues, or enantiomers.

The target analyte(s) may include a fatty acid or derivative thereof, for example, an esterified fatty acid. The ester may be a methyl, ethyl, propyl, butyl, pentyl, hexyl, heptyl, octyl, nonyl, or decyl ester. In some embodiments, the fatty acid or derivative thereof is selected from one or more of docosahexaenoic acid, crotonic acid, myristoleic acid, palmitoleic acid, sapienic acid, oleic acid, elaidic acid, vaccenic acid, gadoleic acid, eicosenoic acid, erucic acid, nervonic acid, linoleic acid, eicosadienoic acid, docosadienoic acid, linolenic acid, pinolenic acid, eleostearic acid, mead acid, dihomo-γ-linolenic acid, eicosatrienoic acid, stearidonic acid, arachidonic acid, eicosatetraenoic acid, adrenic acid, bosseopentaenoic acid, eicosapentaenoic acid, ozubondo acid, sardine acid, tetracosanolpentaenoic acid, cervonic acid, herring acid, propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, carboceric acid, montanic acid, nonacosylic acid, melissic acid, hentriacontylic acid, lacceroic acid, psyllic acid, geddic acid, ceroplastic acid, hexatriacontylic acid, heptatriacontylic acid, octatriacontylic acid, nonatriacontylic acid, tetracontylic acid, or an esterified derivative thereof.

In one embodiment, the analyte is eicosapentaenoic acid (EPA) or eicosapentaenoic acid ethyl ester (EPA-E). EPA or (5Z,8Z,11Z,14Z,17Z)-5,8,11,14,17-eicosapentaenoic acid has the structure:

[Formula 1]

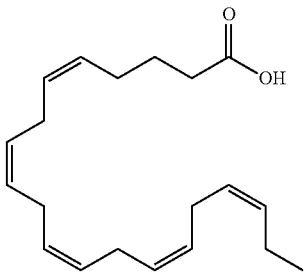

EPA-E (5Z,8Z,11Z,14Z,17Z)-5,8,11,14,17-eicosapentaenoic acid ethyl ester has the structure:

[Formula 2]

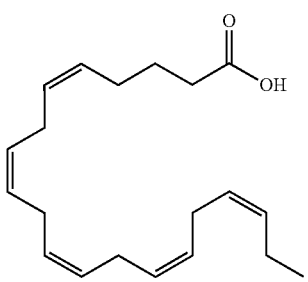

After elution, and evaporation of mobile phase, the analyte may have a purity of greater than about 70%, greater than about 80%, greater than about 85%, greater than about 86%, greater than about 90%, greater than about 95%, greater than about 96.5%, greater than about 98%, greater than about 99%, greater than about 99.5%, greater than about 99.8%, or greater than about 99.9%. In some embodiments, the analyte may have a purity of less than 100% or less than 99.9999%. In some embodiments, the yield is greater than 50%, greater than 55%, greater than 60%, greater than 65%, greater than 70%, greater than 75%, or greater than 80% and/or less than 100%, less than 95%, less than 90% or less than 85%. In some embodiments, the recovery rate is greater than 55%, greater than 60%, greater than 65%, greater than 70%, greater than 75%, greater than 80%, greater than 85%, greater than 90%, greater than 95%, and or less than 100%, less than 99.9%, less than 99.8% or less than 96%.

The retention time of the analyte may be between about 0.5 minutes to about 2 minutes, about 2 minutes to about 4 minutes, about 4 minutes to about 6 minutes, about 6 minutes to about 8 minutes, about 8 minutes to about 10 minutes, about 10 minutes to about 12 minutes, about 12 minutes to about 14 minutes, about 14 minutes to about 16 minutes, about 16 minutes to about 18 minutes, about 18 minutes to about 20 minutes, about 20 minutes to about 22 minutes, about 22 minutes to about 24 minutes, about 24 minutes to about 26 minutes, about 26 minutes to about 28 minutes, about 28 minutes to about 30 minutes, about 30 minutes to about 32 minutes, about 32 minutes to about 34 minutes, about 34 minutes to about 36 minutes, about 36 minutes to about 38 minutes, or about 38 minutes to about 40 minutes or greater than about 0.5 minutes, greater than about 1 minute, greater than about 1.5 minutes, greater than 2 minutes, or greater than 5 minutes and/or less than 50 minutes, less than 40 minutes, less than 30 minutes, or less than 20 minutes.

Internal standards may be added to the sample as a reference marker to determine the relative retention time of the analyte to the internal standard, or to aid in quantitation of the analyte. Internal standards may be appropriately selected by those of ordinary skill in the art to be a compound that is very similar, but not identical to the target analyte, for example, a deuterated derivative of the target analyte. If used for quantitative purposes the internal standard can then be used for calibration by plotting the ratio of the analyte signal to the internal standard signal as a function of the analyte concentration of the standards, wherein a standard is a sample of known concentration prepared by those of skill in the art to use as a reference against the unknown analyte sample being quantitated.

In another aspect, a compound or composition purified by the method described herein is provided. In some embodiments, the compound or composition is or includes a fatty acid or esterified derivative thereof, protein, nucleic acid, or small molecule. In some embodiments, the compound or composition is or includes a fatty acid or an esterified derivative thereof.

In some embodiments, the compound or composition is or includes docosahexaenoic acid, crotonic acid, myristoleic acid, palmitoleic acid, sapienic acid, oleic acid, elaidic acid, vaccenic acid, gadoleic acid, eicosenoic acid, erucic acid, nervonic acid, linoleic acid, eicosadienoic acid, docosadienoic acid, linolenic acid, pinolenic acid, eleostearic acid, mead acid, dihomo-γ-linolenic acid, eicosatrienoic acid, stearidonic acid, arachidonic acid, eicosatetraenoic acid, adrenic acid, bosseopentaenoic acid, eicosapentaenoic acid, ozubondo acid, sardine acid, tetracosanolpentaenoic acid, cervonic acid, herring acid, propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, carboceric acid, montanic acid, nonacosylic acid, melissic acid, hentriacontylic acid, lacceroic acid, psyllic acid, geddic acid, ceroplastic acid, hexatriacontylic acid, heptatriacontylic acid, octatriacontylic acid, nonatriacontylic acid, tetracontylic acid, or an esterified derivative thereof.

In some embodiments, the esterified derivative thereof is a methyl, ethyl, propyl, butyl, pentyl, hexyl, heptyl, octyl, nonyl, or decyl ester. In some embodiments, the compound is eicosapentaenoic acid ethyl ester.

In some embodiments, the compound or composition may have a purity of greater than about 70%, greater than about 80%, greater than about 85%, greater than about 86%, greater than about 90%, greater than about 95%, greater than about 96.5%, greater than about 98%, greater than about 99%, greater than about 99.5%, greater than about 99.8%, or greater than about 99.9%. In some embodiments, the compound or composition may have a purity of less than about 100% or less than about 99.9999%. In some embodiments, the compound or composition may be obtained in a yield that is greater than 50%, greater than 55%, greater than 60%, greater than 65%, greater than 70%, greater than 75%, or greater than 80%. In some embodiments, the compound or composition may have a yield that is less than 100%, less than 95%, less than 90% or less than 80%. In some embodiments, the compound or composition may have a recovery rate that is greater than 55%, greater than 60%, greater than 65%, greater than 70%, greater than 75%, greater than 80%, greater than 85%, greater than 90%, greater than 95%, greater than 98%, greater than 99%, or greater than 99.7%. In some embodiments, the compound or composition may have a recovery rate that is less than 100%, less than 99.9999%.

In some embodiments, when the composition includes a fatty acid or esterified derivative thereof, it may include one or more components other than the main component. The component other than the main component may be included in the composition at an amount of equal to or less than about 30%, equal to or less than about 20%, equal to or less than about 15%, equal to or less than about 14%, equal to or less than about 10%, equal to or less than about 5%, equal to or less than about 4.5%, equal to or less than about 4%, equal to or less than about 3.5%, equal to or less than about 2%, equal to or less than about 1%, equal to or less than about 0.5%, equal to or less than about 0.2%, or equal to or less than about 0.1%. When the main component is a fatty acid ester, examples of components other than the main component include other fatty acid esters. When the main component is eicosapentaenoic acid ester, examples of other components include docosahexaenoic acid ester, and other esters of fatty acids given as examples in the present specification. When the main component is docosahexaenoic acid ester, examples of other components include eicosapentaenoic acid ester, and other esters of fatty acids given as examples in the present specification.

In some embodiments, the composition may include two components at a total content of a certain level or higher. The total content may be, for example, greater than about 70%, greater than about 80%, greater than about 85%, greater than about 86%, greater than about 90%, greater than about 95%, greater than about 96.5%, greater than about 98%, greater than about 99%, greater than about 99.5%, greater than about 99.8%, or greater than about 99.9%.

In some embodiments, when the composition includes fatty acids or esterified derivatives thereof as the two components at a total content of a certain level or higher, the composition may include one or more components other than the two components contained at a total content of a certain level or higher. The component other than the two components contained at a total content of a certain level or higher may be included in the composition at an amount of equal to or less than about 30%, equal to or less than about 20%, equal to or less than about 15%, equal to or less than about 14%, equal to or less than about 10%, equal to or less than about 5%, equal to or less than about 4.5%, equal to or less than about 4%, equal to or less than about 3.5%, equal to or less than about 2%, equal to or less than about 1%, equal to or less than about 0.5%, equal to or less than about 0.2%, or equal to or less than about 0.1%. When the two components contained at a total content of a certain level or higher are two fatty acid esters, examples of components other than the two components include other fatty acid esters. When the main components are eicosapentaenoic acid ester and docosahexaenoic acid ester, examples of other components include other esters of fatty acids given as examples in the present specification.

Some embodiments of the present disclosure are directed to methods of purifying one or more compounds by column chromatography comprising: adding a stationary phase to a column, and allowing a slurry comprising the stationary phase to stand in the column for a standing time.

Some embodiments of the present disclosure are directed to methods of packing a chromatography column comprising: adding a stationary phase to a column, and allowing a slurry comprising the stationary phase to stand in the column for a standing time.

Some embodiments of the present disclosure are directed to methods of increasing theoretical plate number (N) in a column chromatography comprising: adding a stationary phase to a column, and allowing a slurry comprising the stationary phase to stand in the column for a standing time, wherein the increase in N is relative to a column chromatography without standing time or wherein the increase in N is relative to a slurry that is allowed to stand for a reduced standing time that is less than the standing time.

Some embodiments of the present disclosure are directed to methods of improving symmetry factor of a chromatographic peak in column chromatography comprising allowing a slurry to stand in the column for a standing time, wherein the improvement comprises decreasing the symmetry factor of the peak to a quantity $\geq 1$, and wherein the decrease is relative to a symmetry factor when a column chromatography comprises a reduced standing time that is absent or less than the standing time and the symmetry factor is >1; or the improvement comprises increasing the symmetry factor of the peak to a quantity $\leq 1$, and wherein the increase is relative to a symmetry factor when the column chromatography comprises a reduced standing time that is absent or less than the standing time and the symmetry factor is <1. In some embodiments, all chromatography conditions other than standing time are identical when the column chromatography comprises the standing time and when the column chromatography comprises the reduced standing time that is absent or less than the standing time.

In some embodiments of these methods, the column is under atmospheric pressure during standing time. In some embodiments of these methods, pressure is applied to the column after standing time. In some embodiments of these methods, each standing time is independently between about 0.5 minutes to about 2 minutes, about 2 minutes to about 4 minutes, about 4 minutes to about 6 minutes, about 6 minutes to about 8 minutes, about 8 minutes to about 10 minutes, about 10 minutes to about 12 minutes, about 12 minutes to about 14 minutes, about 14 minutes to about 16 minutes, about 16 minutes to about 18 minutes, about 18 minutes to about 20 minutes, about 20 minutes to about 22 minutes, about 22 minutes to about 24 minutes, about 24 minutes to about 26 minutes, about 26 minutes to about 28 minutes, about 28 minutes to about 30 minutes, about 30 minutes to about 32 minutes, about 32 minutes to about 34 minutes, about 34 minutes to about 36 minutes, about 36 minutes to about 38 minutes, or about 38 minutes to about 40 minutes. In some embodiments, the standing time is independently between about 0.5 minutes to about 5 minutes, about 5 minutes to about 10 minutes, about 10 minutes to about 15 minutes, about 15 minutes to about 20 minutes, about 20 minutes to about 25 minutes, about 25 minutes to about 30 minutes, about 30 minutes to about 35 minutes, about 35 minutes to about 40 minutes, about 40 minutes to about 45 minutes, about 45 minutes to about 50 minutes, about 50 minutes to about 55 minutes, about 55 minutes to about 60 minutes, about 60 minutes to about 65 minutes, about 65 minutes to about 70 minutes, about 70 minutes to about 75 minutes, about 75 minutes to about 80 minutes, about 80 minutes to about 85 minutes, about 85 minutes to about 90 minutes, about 90 minutes to about 95 minutes, or about 95 minutes to about 100 minutes, about 100 minutes to about 105 minutes, about 105 minutes to about 110 minutes, about 110 minutes to about 115 minutes, about 115 minutes to about 120 minutes.

In some embodiments of these methods, all chromatography conditions other than sedimentation volume are identical when the column chromatography comprises the decreased sedimentation volume and when the column chromatography is performed with a column packed with fresh slurry. In some embodiments of these methods, the fresh slurry comprises a mobile phase (or solvent) and a stationary phase combined for more than about 0.5 minutes, 1 minute, 2 minutes, 5 minutes, 10 minutes, 20 minutes, 30 minutes, 40 minutes, 50 minutes, 60 minutes, 70 minutes, 80 minutes, 90 minutes, 100 minutes, 110 minutes, 120 minutes and/or less than 200 minutes, 185 minutes, 175 minutes, 165 minutes, 155 minutes, 145 minutes, 135 minutes, 125 minutes, 115 minutes, 105 minutes, 95 minutes, 85 minutes, 75 minutes, 65 minutes, 55 minutes, 45 minutes, 35 minutes, 25 minutes. Combining the mobile phase (or solvent) and the stationary phase includes agitation. In some embodiments of these methods, the decrease in sedimentation volume is over an amount of time between about 0 minutes to about 2 minutes, about 2 minutes to about 4 minutes, about 4 minutes to about 8 minutes, about 8 minutes to about 16 minutes, about 16 minutes to about 24 minutes, about 24 minutes to about 32 minutes, about 32 minutes to about 50 minutes, about 50 minutes to about 70 minutes, about 70 minutes to about 90 minutes, about 90 minutes to about 110 minutes, about 110 minutes to about 130 minutes, about 130 minutes to about 150 minutes. In some embodiments of these methods, the sedimentation volume remains substantially constant after the amount of time. In some embodiments of these methods, the decrease in sedimentation volume is over a standing time. In some embodiments of these methods, wherein decreasing sedimentation volume comprises allowing the mixture to stand at atmospheric pressure. In some embodiments of these methods, pressure is applied to the column after the decrease in sedimentation volume. In some embodiments of these methods, the column is an axial compression column. In some embodiments of these methods, the slurry comprises a stationary phase and one or more of water, methanol, ethanol, acetonitrile, ethyl acetate, hexanes, or dichloromethane. In some embodiments of these methods, the slurry comprises methanol. In some embodiments of these methods, the stationary phase comprises particles of C30, C22, C18, C8, C5, C4, biphenyl, fluorophenyl, hydrophilic interaction liquid chromatography (HILIC) stationary phase, acrylamide, silica, phenyl-hexyl stationary phase, polar embedded alkyl, and/or fluorophenyl propyl. In some embodiments of these methods, the stationary phase is particles of C18.

The settling during the standing time preferable occurs at atmospheric pressure (about 0.101325 MPa). In some embodiments, the pressure during standing time is between about 0.1 MPa to about 0.2 MPa, about 0.2 MPa to about 0.4 MPa, about 0.4 MPa to about 0.6 MPa, about 0.6 MPa to about 0.8 MPa, or about 0.8 MPa to about 1 MPa. In some embodiments, the pressure during standing time is less than about 0.1 MPa. In some embodiments, the pressure during standing time is atmosphere pressure. In some embodiments, the pressure during standing time is greater than 0.01 MPa, greater than 0.05 MPa, or greater than 0.1 MPa and/or less than 1 MPa, less than 0.8 MPa, less than 0.6 MPa, less than 0.4 MPa or less than 0.2 MPa.

In another aspect, a method of increasing theoretical plate number (N) in a column chromatography is provided comprising allowing a slurry to stand in the column for a standing time, wherein the increase is relative to a column chromatography without standing time or wherein slurry stands for a reduced standing time that is less than the standing time.

In another aspect, a method of improving symmetry factor(S) of a chromatographic peak in column chromatography is provided comprising allowing a slurry to stand in the column for a standing time, wherein the improvement comprises decreasing the symmetry factor of the peak to a quantity $\geq 1$, and wherein the decrease is relative to a symmetry factor when a column chromatography comprises a reduced standing time that is absent or less than the standing time and the symmetry factor is >1; or the improvement comprises increasing the symmetry factor of the peak to a quantity $\leq 1$, and wherein the increase is relative to a symmetry factor when a column chromatography comprises a reduced standing time that is absent or less than the standing time and the symmetry factor is <1.

In some embodiments, the sedimentation volume ratio (sedimentation volume ratio (%)=sedimentation volume (ml)/ODS volume (ml)×100) is substantially constant at the completion of standing time. The sedimentation volume ratio may decrease upon addition of slurry to the column until reaching a constant value at completion of the standing time. In some embodiments the sedimentation volume ratio decreases to between about 150% to about 140%, about 140% to about 130%, about 120% to about 110%, or about 110% to about 100%. In some embodiments the sedimentation volume ratio decreases to less than about 160%, less than about 150%, less than about 140% or less than about 130% and/or more than about 100% or more than about 105%.

In some embodiments, the standing time results in improvement of performance, e.g., increased N, S approaching 1, increased yield or retention, and/or decreased sedimentation volume, and is between about 15 and about 25 minutes, about 18 and about 22 minutes, or is about 20 minutes. In some embodiments, each standing time is independently between about 0.5 minutes to about 5 minutes, about 5 minutes to about 10 minutes, about 10 minutes to about 15 minutes, about 15 minutes to about 20 minutes, about 20 minutes to about 25 minutes, about 25 minutes to about 30 minutes, about 30 minutes to about 35 minutes, about 35 minutes to about 40 minutes, about 40 minutes to about 45 minutes, about 45 minutes to about 50 minutes, about 50 minutes to about 55 minutes, about 55 minutes to about 60 minutes, about 60 minutes to about 65 minutes, about 65 minutes to about 70 minutes, about 70 minutes to about 75 minutes, about 75 minutes to about 80 minutes, about 80 minutes to about 85 minutes, about 85 minutes to about 90 minutes, about 90 minutes to about 95 minutes, or about 95 minutes to about 100 minutes, about 100 minutes to about 105 minutes, about 105 minutes to about 110 minutes, about 110 minutes to about 115 minutes, about 115 minutes to about 120 minutes. In some embodiments, each standing time is independently more than about 0.5 minutes, 1 minute, 2 minutes, 5 minutes, 10 minutes, 20 minutes, 30 minutes, 40 minutes, 50 minutes, 60 minutes, 70 minutes, 80 minutes, 90 minutes, 100 minutes, 110 minutes, 120 minutes, 130 minutes, 140 minutes, 150 minutes, 200 minutes, 300 minutes, 400 minutes, 500 minutes, 600 minutes, 1200 minutes, 1440 minutes, 2880 minutes and/or less than 200 minutes, 185 minutes, 175 minutes, 165 minutes, 155 minutes, 145 minutes, 135 minutes, 125 minutes, 115 minutes, 105 minutes, 95 minutes, 85 minutes, 75 minutes, 65 minutes, 55 minutes, 45 minutes, 35 minutes, 25 minutes, 15 minutes, 5 minutes, 3 minutes. Longer standing time may provide better symmetry factor and/or theoretical plate number while shorter setting time may provide increased ease of preparation of the column, which may result in increased productivity. One may choose suitable standing time for desired purpose.

A fresh slurry will have a sedimentation volume ratio higher than the sedimentation volume ratio of the slurry at completion (or during progression of settling) of standing time. In some embodiments, the sedimentation volume ratio of fresh slurry may be decrease to between about 200% to about 180%, about 180% to about 160%, about 160% to about 140%, about 140% to about 130%, about 130% to about 120%, or about 120% to about 110%. In some embodiments, the sedimentation volume ration of fresh slurry may be decrease greater than about 100%, greater than about 110%, greater than about 120% or greater than about 130% and/or less than about 200%, less than about 180%, or less than about 160%.

The method may further comprise packing the column. Packing is preferably performed at the completion of standing time and/or when sedimentation volume decreases and remains substantially constant. Packing may comprise applying a packing pressure to the settled slurry and compressing the slurry within the column. In one embodiment, the packing pressure is a value that includes the atmospheric pressure. The packing pressure may be between about 0.1 MPa to about 0.5 MPa, about 0.5 MPa to about 1 MPa, about 1 MPa to about 1.5 MPa, about 1.5 MPa to about 2 MPa, about 2 MPa to about 2.5 MPa, about 3 MPa to about 3.5 MPa, about 3.5 MPa to about 4 MPa, about 4 MPa to about 4.5 MPa, about 4.5 MPa to about 5 MPa, about 5 MPa to about 5.5 MPa, about 5.5 MPa to about 6 MPa, about 6 MPa to about 6.5 MPa, about 6.5 MPa to about 7 MPa, about 7 MPa to about 7.5 MPa, about 7.5 MPa to about 8 MPa, about 8 MPa to about 8.5 MPa, about 8.5 MPa to about 9 MPa, or about greater than about 9 MPa. In some embodiments, the packing pressure is about 3.0 MPa to about 6.0 MPa. In some embodiments, the packing pressure is greater than about 0.1 MPa, greater than about 0.5 MPa, greater than about 1 MPa, greater than about 2 MPa or greater than about 3 MPa and/or less than about 10 MPa, less than about 9 MPa, less than about 8 MPa, less than about 7 MPa or less than about 6 MPa. The slurry may be compressed during packing and the column vented.

DEFINITIONS

"Liquid chromatography" (LC) or "column chromatography" as used herein means a process of selective retention or retardation of one or more components of a fluid solution as the fluid flows through a column containing stationary material(s) made of a finely divided substance and/or a material having capillary passageways. Retention results from the relative partitioning of the components of the mixture between the stationary phase and the bulk fluid phase (e.g., mobile phase), the later of which moves through the stationary materials. LC is used for analysis and separation of mixtures of two or more substances. LC includes, for example, high turbulence liquid chromatography (HTLC), preparative chromatography, analytical chromatography (e.g., HPLC), simulated moving bed chromatography, actual moving bed chromatography and supercritical fluid chromatography (SFC).

"High turbulence liquid chromatography" (HTLC) as used herein refers to the use of turbulent flow to enhance the rate of mass transfer during column chromatography, improving the separation characteristics provided. This is in contrast to traditional HPLC analysis which relies on column packings in which laminar flow of the sample through the column is the basis for separation of the analyte of interest from the test sample. HTLC has been applied for sample preparation to detect drugs prior to analysis by mass spectrometry. See, e.g., Zimmer et al., *J. Chromatogr.* A 854:23-35 (1999); see also, U.S. Pat. Nos. 5,968,367; 5,919,368; 5,795,469; and 5,772,874.

The terms "nonpolar" and "polar" to describe mobile phase solvents or analytes, may be used as terms of relativity towards each other. For example "nonpolar" may refer to the solvent in the mobile phase which is least polar, while "polar" may refer to the solvent in the mobile phase which is more polar than the "nonpolar" solvent.

"Preparative chromatography" as used herein refers to coarse separation of a particular analyte from a mixture containing other substances that are grossly different or even similar to the analyte (e.g., a small molecule analyte may be separated from a mixture containing proteins and other large molecular weight species). Such methods involve the selective retention of a particular solute or analyte in a complex mixture by a column, while other components are not retained. The analyte is then selectively removed from the column and may be collected for further use or analysis. Preparative chromatography does not necessarily involve large samples, or large columns (although very large columns are often used in preparative chromatography). In preparative chromatography, column diameters can range from a few millimeters to a meter or more, and mobile phase volumes may range from a few milliliters to hundreds of liters. In preparative chromatography, analytes eluted from the column may be collected in an in-line reservoir (e.g., sample loop or tubing) or in reservoirs as fractions. Alternatively, analytes, following elution from the preparative column, may be directed to an in-line analytical column or directly to a detector for further analysis.

"Analytical chromatography" as used herein refers to a fine separation of closely related molecules (e.g., molecules of similar molecular weights). In analytical chromatography, analytes separated on a column, eluted from the column, and monitored or detected. The term "analytical column" as used herein refers to a chromatography column having sufficient chromatographic plates to effect a separation of an analyte from other materials in a sample, wherein such a separation is sufficient to allow detection and determination of the presence or amount of the analyte.

"Analyte" as used herein, refers to one or more target substances to be purified, or isolated from a mixture of other components.

Figure 2:
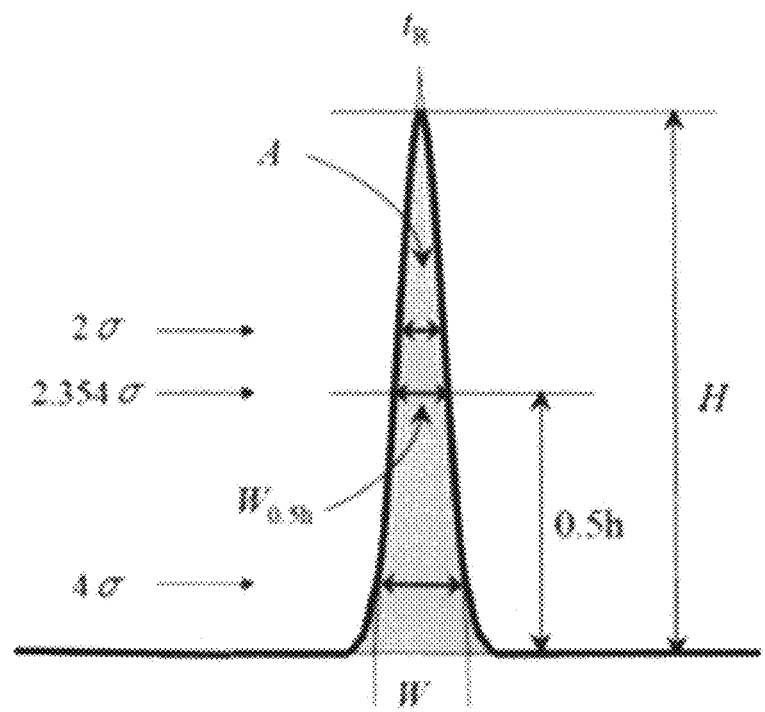
FIG. 2 shows a chromatographic peak with variables used to calculate theoretical plate number (N). σ is the standard deviation. W is peak width. A is peak area. $W_{0.5h}$ is peak full width at half maximum (FWHM). H is peak height.
Figure 3:
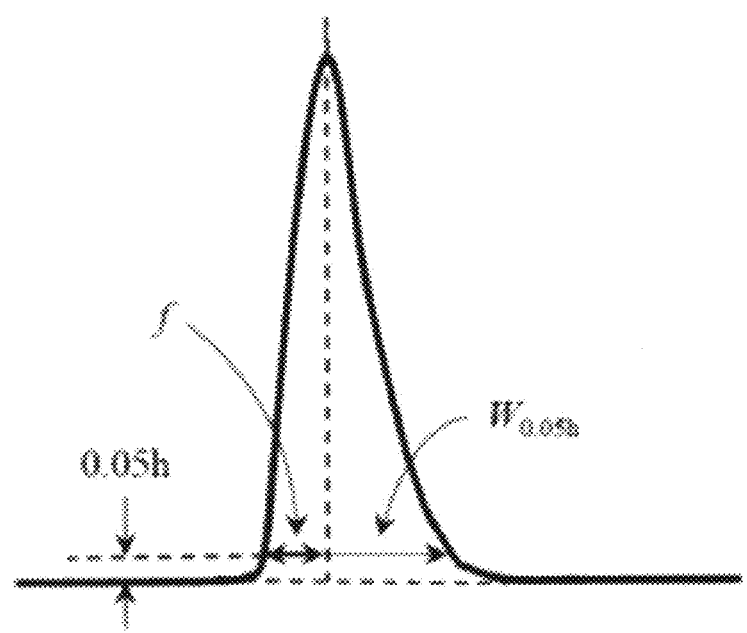
FIG. 3 shows a chromatographic peak with variables used to calculate symmetry factor ($As_{0.05}$ or S). $W_{0.05h}$ is peak width at ½0th the peak height above peak baseline. When a vertical line drawn from the peak apex dissects a horizontal line drawn at ½0th the peak height above peak baseline ($W_{0.5h}$), the distance along the horizontal line from the leading edge of the peak to the vertical line is f or $A_{0.05h}$.

"Peak" as used herein refers to a peak in a chromatogram. A chromatogram is a plot showing signal detected by a detector over time. As analytes are detected by the detector, the signal increases, and the chromatogram displays a "peak," as shown in FIGS. 2 and 3. Each peak in the chromatogram indicates the presence of a chemical in the sample. Each peak is labeled with a retention time and time in the chromatogram increases from left to right.

"Separating" as used herein, refers to the process characterized by the spatial separation of the components of a mixture, including analytes, based on their partitioning differential between phases (e.g., mobile and stationary phases) in relative motion. Separating results from loading the sample onto the column and elution of the column following loading.

"Fractionation" is a separation process in which a certain quantity of a mixture is divided during a phase transition, into a number of smaller quantities in which the composition varies according to a gradient. Different fractions are collected at different timepoints based on differences in a specific property of the individual components (analytes within the mixture or sample), for example, its affinity for stationary phase and/or mobile phase.

"Loading" as used herein, refers to the application of a sample containing analyte to the column until the entire sample is contained within the column. The sample is typically loaded onto the top of the stationary phase of the packed column. Wherein the "top" is the end of stationary phase first receiving mobile phase as it elutes through the column. Loading may be accomplished by injectors, pumps, or direct application of sample to the top of the stationary phase. Sample may be mixed with a minimal amount of mobile phase or other solvent for loading, loaded directly neat, or dry loaded with stationary phase. Dry loading corresponds to mixing the sample with a slurry and evaporating all liquid from the slurry, then loading the dry mixture of sample and stationary phase onto the top of the column's packed stationary phase.

"Eluting" as used herein, refers to the process of flowing solvent (e.g., mobile phase) through the column after loading so as to remove substances not adsorbed on the column or substances from which the analyte is to be separated. Multiple elutions are possible using different mobile phases.

"Theoretical plate number" (N) is an index that indicates column efficiency. It describes the number of plates as defined according to plate theory, and can be used to determine column efficiency based on calculation in which the larger the theoretical plate number the sharper the peaks. The theoretical plate number is included as a numerical value in column instruction manuals and inspection reports. Assuming a Gaussian distribution (normal distribution), the theoretical plate number is represented by the equation (1) below, wherein the variables are as defined in the description of FIG. 2:

[Formula 3]

$$N = \left(\frac{t_R}{\sigma}\right)^2. \quad (1)$$

"Symmetry factor" or "tailing factor" (S) is a coefficient that shows the degree of peak symmetry. It is represented in equation (2) below based on the variables as defined in the description of FIG. 3. If S >1 there is peak tailing. If S=1 there is peak symmetry (Gaussian distribution). If S<1 there is a leading peak (reverse tailing). "Peak tailing" as illustrated in FIG. 4 refers to elongation of the trailing edge of the chromatographic peak.

[Formula 4]

$$S = \frac{W_{0.05h}}{2f}. \quad (2)$$

"Settled stationary phase" refers to a sedimentation layer formed by letting the stationary phase contained in the slurry settle. A sedimentation layer typically forms at the bottom surface of the column after slurry is added to or formed in the column.

"Sedimentation volume" refers to the volume occupied by the sedimentation layer formed by letting the stationary phase contained in the slurry settle.

"Packed layer of stationary phase" refers to a layer obtained by compressing at a packing pressure the sedimentation layer formed by letting the stationary phase contained in the slurry settle.

"Volume of packed layer of stationary phase" refers to the volume occupied by the packed layer of stationary phase obtained by compressing the sedimentation layer at a packing pressure.

"Column including a packed layer of stationary phase" refers to a column formed by introducing a slurry containing the stationary phase, letting the stationary phase contained in the slurry settle to form a sedimentation layer, and applying a packing pressure to the sedimentation layer to form a packed layer of stationary phase in column chromatography.

"Sedimentation rate" refers to the rate at which sediment of stationary phase is formed in the slurry over time upon standing.

"Slurry" refers to a mixture of stationary phase and liquid. Liquid is preferably a mobile phase (or solvent), and the stationary phase is preferably particles. In some embodiments the slurry is a viscous liquid comprising mobile phase (or solvent) with stationary phase suspended therein. It will be understood that a solvent may be any solvent suitable for forming a slurry, and includes the solvents disclosed herein for mobile phases (e.g., one or more of water, methanol, ethanol, acetonitrile, ethyl acetate, hexanes, dichloromethane or any other appropriate solvent known in the art). It will also be understood that, in some embodiments, the solvent in the slurry is a different solvent from what is used as the mobile phase.

"Slurry concentration" refers to the mass or volume of stationary phase per unit volume of mobile phase for a slurry.

A "packed" column or "packing" a column refers to the process comprising adding a stationary phase to a column to prepare a slurry, or adding a slurry comprising a stationary phase in liquid to a column, and applying pressure to the slurry in the column. In one embodiment, chromatography which comprises packing may be performed using a movable stopper-type column. Applying the pressure may compress the stationary phase prior to chromatography. In some embodiments, the process of applying pressure to the slurry in the column is performed after a settling time, preferably the settling time is at atmospheric pressure and the aforementioned process is done above atmospheric pressure. In some embodiments, the process of applying pressure to the slurry in the column is performed after a standing time, preferably the standing time is at atmospheric pressure and the aforementioned process is done above atmospheric pressure.

"Standing time", with respect to slurry packing, in which a slurry formed by premixing the stationary phase and the mobile phase is introduced into an empty column, refers to the time during which a slurry is allowed to stand from immediately after the whole slurry has been introduced into the column. In this case, the standing time starts immediately after completing the introduction of the whole slurry. Further, in dry packing in which the mobile phase is introduced into the empty column before introducing the stationary phase, "standing time" refers to the time during which a slurry generated by the introduction of the stationary phase is allowed to stand from immediately after the whole stationary phase has been introduced into the column. In this case, the standing time starts immediately after completing the introduction of the stationary phase. Further, "interval standing time" refers to the time during which a slurry is allowed to stand from immediately after a part of the slurry or the stationary phase has been introduced into the column, when the slurry or stationary phase is introduced in parts. In this case, the interval standing time starts immediately after completing the introduction of a part of a slurry or a stationary phase. The stationary phase in the slurry settles during the standing time. Furthermore, the standing time ends at the time the pressure increases relative to the slurry in a state of being left standing. In another embodiment, the standing time ends at the time the mobile phase is discharged from the column. As used herein, a standing time is the time for settling the stationary phase after introduction into the column, and it corresponds to the settling time.

"Biphenyl," "C30," "C22," "C18," "C8," "C5," "C4" as used herein refer to functional groups present on a column packing material (stationary phase). For example, a biphenyl column exposes the material flowing through the column to unsubstituted biphenyl groups, while a C18 column exposes the material flowing through the column (e.g., mobile phase and analytes) to unsubstituted straight or branched chain 18-carbon alkyl groups.

"Fresh" in regards to describing a slurry, refers to a slurry that has been recently prepared, e.g., a slurry 1 minute after, 5 minutes after, 10 minutes after, 15 minutes after, 20 minutes after, 40 minutes after, 60 minutes after, 120 minutes after, 180 minutes after, 240 minutes after, 300 minutes after, 360 minutes after, 480 minutes after, 960 minutes after, 1440 minutes after completion of mixing the mobile phase (or solvent) and the stationary phase.

An "axial compression column" includes a movable piston attached to a hydraulic jack. The piston is used to pack the column and keeps the stationary phase under dynamic (and adjustable) compression as illustrated in Step 3 of FIG. 1.

"Settle" or "settling" refers to the process of allowing a slurry to rest, unagitated. In some embodiments, settling is performed at atmospheric pressure. In some embodiments settling is performed at a pressure less than the pressure applied during packing.

"Chromatography conditions" refer to parameters under which chromatography is run. Examples include, packing pressure, mobile phase and stationary phase composition, slurry concentration, pressure under which the column is run, mobile phase gradient, mobile phase flow rate, column type used, detection instrumentation and parameters used, sample preparation protocol employed, settling time, and pressure at which settling is performed, standing time, and pressure at which the slurry is allowed to stand.

"Gradient" refers to a change in mobile phase composition over time during column chromatography. As solvent is eluted through the column the composition of the mobile phase may change. A different mobile phase me be added in increasing percentage over time during elution.

"Purity" is the ratio showing the content of the main component of the composition, and it may be calculated from the measurement result of GC using an internal standard.

"Product" refers to the desired composition obtained from a single fraction or a combination of plurality of fractions obtained by elution and fractionation.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. In some embodiments, about may refer to ±5%, ±2.5%, or ±1% of the number to which it refers.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

This invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends and advantages inherent herein. The present examples, along with the methods described herein are presently representative of embodiments and are exemplary, and are not intended as limitations on the scope of the disclosure. Changes therein and other uses which are encompassed within the spirit of the disclosure as defined by the scope of the claims will occur to those skilled in the art.

EXAMPLES

Example 1: Column Packing

The solid phase used for the column was ODS-SQ (reverse phase C18), specifically KE-ODSSQ (YMC CO., LTD., average particle size 50 μm, specific surface area 350).

For the axial compression column, a movable stopper-type preparative column (model number DAU700S) manufactured by YMC Co., Ltd. was used. The inner diameter was 50 mm. Slurry parameters depended on the amount of methanol solvent used (Kanto Chemical Co., LTD., methanol for high performance liquid chromatography) with 295 g of ODS. Packing solvent volume and packing height (300 mm) were selected as described in the instruction manual. The concentration for the slurry was adjusted as follows: Slurry concentration (%)=ODS (g)/methanol (ml)×100. When the slurry concentration was 42%, 49% or 59%, 700 ml, 600 ml or 500 ml of methanol was mixed with 295 g of ODS weight.

First, slurry charging was studied as a filling method. 295 g of powdered ODS was placed in a 1 liter beaker, methanol was added, and the mixture was agitated with a glass rod for 5 minutes to prepare a slurry. The slurry in a suspended state was added from the top of the empty column. An embodiment of this process is illustrated, e.g., in Step 1 of FIG. 1. In the case of dry charging, methanol was added to the column in advance, and then ODS was added portion-wise from the top of the column. In each case, after ODS was introduced to the column, filling was performed by applying a packing pressure of 4 MPa. Performance testing of the further Examples was performed after eluting 2 bed volumes of methanol through the column.

Example 2: Theoretical Plate Number and Symmetry Factor

The ODS-SQ packed columns of Example 1 was performance tested to calculate theoretical plate number and symmetry factor for each packing technique for the latter examples. The HPLC instrument used was the K-Prep Lab300S (YMC Co., LTD). The movable stopper-type preparative column used was the DAU700S (YMC Co., LTD). The flow rate was 65 ml/minutes. The linear velocity was 2 m/hr. Solvent was methanol of HPLC grade (Kanto Chemical Co., LTD.). The analyte purified was eicosapentaenoic acid ethyl ester (EPA-E) which was dissolved at 0.4% in methanol (w/v). 1 ml of this was used to load the column.

The EPA-E was previously prepared as follows: crude sardine oil was subjected to short path distillation (SPD). The SPD oil was subjected to ethanolysis reaction with ethyl alcohol in the presence of an alkali catalyst to form a fish oil ethyl ester, EPA-E. The fish oil ethyl ester was then purified using the rectification and the above described HPLC column of reverse-phase distribution type (ODS). The solvent was subsequently distilled off to yield EPA-E at an area percentage of 97%.

The conditions used for the GC analysis were as follows.
GC: 6890N (Agilent Technologies)
Column: DB-WAX (Agilent Technologies)
30 m×0.25 mm ID, 0.25 μm film thickness
Carrier gas: adjusted to a rate that provides EPA at 13 min.
Inlet: 250° C., 1 μL, Split (1:50)
Column temperature: 210° C. isothermic
Detector: FID, 260° C.
Makeup gas: Nitrogen 40 mL/min.

The theoretical plate number and symmetry factor for the EPA-E was then calculated. Three trials of purification were undertaken, the results of each trial were calculated as described and the mean taken. The theoretical plate number was calculated using the half peak-width method. The formula used for theoretical plate number was:

$$\text{Theoretical plate number (N/m)} = 5.54 \times (tr/W_{0.5h})^2 / \text{column length (m)}$$

wherein tr is retention time and W0.5h is peak width at 50% of height of peak as illustrated in FIG. 2.

The formula used for the symmetry factor calculation was:

$$\text{Symmetry factor } (As_{0.05}) = W_{0.05h}/(2 \times A_{0.05})$$

wherein $W_{0.05h}$ is the peak width at 5% of the height of the peak and $A_{0.05}$ (also referred to as "f" in equation (2) herein) is the peak width of the first half of the peak measured as the horizontal distance from the point of the beginning of the peak (leading edge) to the apex of the peak amplitude (e.g., to the y-axis (perpendicular) running through the peak apex), at 5% of the peak height, this measurement is described in the description, e.g., of FIG. 3.

Example 3: Effect of Standing Time on Column Performance

The standing time after introducing ODS-SQ into the column was examined to determine its effects on theoretical plate number and symmetry factor (calculated as described in Example 2). The column was run at slurry concentrations of 42% or 59% ODS weight/methanol volume. In the ODS manufacturer's instruction manual it does not instruct to allow a standing time after introducing ODS or a slurry containing ODS.

From immediately after introducing the separately prepared slurry, the column was allowed to stand for 30 minutes or 120 minutes, and then a performance test was performed on the column. The results are shown in Tables 1-3. As shown in Tables 1-2, the number of theoretical plates was higher when left standing, and as shown in Table 3, the peak symmetry approached 1. This is thought to be because ODS settled and was allowed to fill evenly.

During the experiment, column density was calculated by the amount of ODS in a column, inner diameter of a column and a height of ODS and found to be no difference after 30 minutes standing, no standing followed by application of packing pressure and 30 minutes standing followed by application of packing pressure.

TABLE 1

| | | | |
|---|---|---|---|
| Slurry conc. (Slurry %) | 42 | 42 | 42 |
| Standing time (min) | 0 | 30 | 120 |
| Theoretical plate number | 2533 | 2917 | 3187 |

TABLE 2

| Slurry conc. (Slurry %) | 59 | 59 | 59 |
|---|---|---|---|
| Standing time (min) | 0 | 30 | 120 |
| Theoretical plate number | 2757 | 3287 | 3673 |

TABLE 3

| Slurry conc. (Slurry %) | 42 | 42 | 42 | 59 | 59 | 59 |
|---|---|---|---|---|---|---|
| Standing time (min) | 0 | 30 | 120 | 0 | 30 | 120 |
| Symmetry factor | 1.66 | 1.48 | 1.23 | 1.42 | 1.22 | 1.03 |

Example 4: Effect of Dry Filling on Peak Performance

Dry charging of ODS-SQ was studied as a filling method with the concentration of 49%. The other conditions were the same as slurry charging described in Example 1 and 2. The results are shown in Table 4.

TABLE 4

| ODS SQ conc. (Dry %) | 49 | 49 |
|---|---|---|
| Standing time (min) | 0 | 30 |
| Theoretical plate number | 2533 | 3267 |
| Symmetry factor | 1.65 | 1.52 |

Example 5: Effect of Interval Standing Time on Column Performance

The interval standing time from immediately after introducing ODS-SQ into the column was examined to determine its effects on theoretical plate number and symmetry factor (calculated as described in Example 2). The column was run at a slurry concentration of 42%, according to the procedure described in Example 1, and at 4 MPa of packing pressure. In the ODS manufacturer's instruction manual it does not instruct to allow a standing time after introducing ODS or the slurry containing ODS.

From immediately after half of the slurry was poured, the column was allowed to settle for 30 minutes, and then the remaining half of the slurry was poured and packed without any standing time, and then a performance test was performed on the column. As shown in Table 5, the number of theoretical plates was higher when left standing in the interval, and the peak symmetry approached 1. This is thought to be because at least half of ODS settled and was allowed to fill evenly.

TABLE 5

| ODS-DQ conc. (Slurry %) | 42 | 42 |
|---|---|---|
| Interval standing time (min) | 0 | 30 |
| Theoretical plate number | 2533 | 2671 |
| Symmetry factor | 1.66 | 1.55 |

Example 6: Effect of Standing Time on Column Performance Using a Variety of ODS The standing time after introducing ODS-B (Osaka Soda CO., LTD., Daisopak SP-120-50-ODS-B, average particle size 50 μm), ODS S-20 (YMC CO., LTD., YMC*GEL ODS-AQ-HG 12 nm S-20 μm AQG12S21, average particle size 20 μm), ODS S-10 (YMC CO., LTD., YMC*GEL ODS-AQ-HG 12 nm S-10 μm AQC12S11, average particle size 10 μm), ODS-A (AGC Si-Tech CO., LTD., M.S. GEL C18 (II)-EP-DM-20-100A, average particle size 20 μm) or ODS-Y (YMC CO., LTD., YMC-Omega, YMC*GEL S-20 um OMG 99S21, average particle size 20 μm) into the column was examined to determine its effects on theoretical plate number and symmetry factor (calculated as described in Example 2). The column was run at slurry concentrations of 49% or 59% ODS weight/methanol volume for each ODS. In the ODS manufacturer's instruction manual it does not instruct to allow a standing time after introducing ODS or the slurry containing ODS. The other conditions were the same as slurry charging described in Examples 1 and 2. The results are shown in Tables 6-8.

TABLE 6

| 4 Mpa of packing pressure | ODS-B | | | |
|---|---|---|---|---|
| ODS conc.(Slurry %) | 42 | 42 | 59 | 59 |
| standing time(min) | 0 | 120 | 0 | 120 |
| Theoretical plate number | 2337 | 2813 | 2663 | 3248 |
| Symmetry factor | 1.79 | 1.57 | 1.15 | 0.93 |

TABLE 7

| 6 Mpa of packing pressure | ODS S-20 | | ODS S-10 | |
|---|---|---|---|---|
| ODS conc.(Slurry %) | 42 | 42 | 42 | 42 |
| standing time(min) | 0 | 120 | 0 | 120 |
| Theoretical plate number | 6067 | 6422 | 10811 | 11473 |
| Symmetry factor | 2.06 | 1.90 | 1.95 | 1.80 |

TABLE 8

| 6 Mpa of packing pressure | ODS-A | | ODS-Y | |
|---|---|---|---|---|
| ODS conc.(Slurry %) | 42 | 42 | 59 | 59 |
| standing time(min) | 0 | 120 | 0 | 120 |
| Theoretical plate number | 5257 | 6490 | 7407 | 8396 |
| Symmetry factor | 2.26 | 2.14 | 2.11 | 1.51 |

Example 7: Yield and Recovery Rate

Yield and recovery rate were determined by HPLC fractionation. The conditions for the HPLC fractionation were as follows. The HPLC instrument used was the K-Prep Lab300S (YMC Co., LTD). The dynamic axial compression column used was the DAU-50-700S (YMC Co., LTD). The flow rate was 65 ml/minutes. Solvent was methanol of HPLC grade (Kanto chemical Co., LTD.). Detection was UV at 230 nm. 2.36 g of EPA-E (80%) was loaded at a load rate of 0.8%. The load rate (%)=80% EPA-E (g)/ODS (g)×100. Trials were conducted ODS (KEODS-50-SQ) stationary phases.

The EPA-E was prepared as follows. Crude sardine oil was subjected to short path distillation (SPD). The SPD oil was subjected to ethanolysis reaction with ethyl alcohol in the presence of an alkali catalyst to form a fish oil ethyl ester, EPA-E. The fish oil ethyl ester was refined by rectification to 80% EPA-E.

In both the chromatography without standing time and chromatography with standing time, Fraction (Fr.) 0 was fractionated from immediately after injection to the rise of the EPA-E peak, then Fr. 1 to 38 were fractionated every 10 seconds, and Fr. 39 was then fractioned for 35 minutes. Methanol was distilled off from the collected fractions using a vacuum evaporator, and C23: 0 methyl ester 1 mg/ml hexane solution was added as an internal standard substance, followed by gas chromatography (GC). The amount of elution of compounds in each fraction was calculated from the area ratio between the GC peak area and the internal standard to select fractions that would provide an EPA-E content of 96.5%, and the yield of the product obtained by combining the selected fractions (Fr. 5 to 17 for chromatography without standing time, and Fr. 4 to 17 for chromatography with standing time) and the recovery rate of the EPA-E in the product were determined as follows:

Yield = Weight of the product (g)/load amount (g), $EPA-E$ recovery rate = (Weight of the product (g)×

$EPA-E$ content (96.5%)/(load amount (g)×$EPA-E$ content (80%).

The conditions used for the GC analysis were as follows. The instrument was a 6890N Network GC System (Agilent) with a DB-WAX 30m×0.25 mm×0.25 μm column. The column temperature was 210° C. The injection temperature was 250° C. with a sprit rate of 1:50 and injection volume of 1 μl. An FID detector at 250° C. was used. A carrier gas of helium with a line speed of 31 cm/minutes was used. The results of yield and recovery rate of EPA are shown in Table 9.

TABLE 9

| Slurry conc. (Slurry %) | 59 | 59 |
|---|---|---|
| Standing time (min) | 0 | 120 |
| Yield | 47.8% | 50.8% |
| EPA recovery rate | 54.9% | 70.1% |

A fish oil sample containing EPA-E and DHA-E was prepared as follows. Crude sardine oil and tuna oil were subjected to short path distillation (SPD). The SPD oil was subjected to ethanolysis reaction with ethyl alcohol in the presence of an alkali catalyst to form an ethyl ester (EPA-E 12.99%, DHA-E 10.44%). The ethyl esters were refined by rectification to 36.40% of EPA-E and 30.60% of DHA-E. 5.0 g and was loaded at a load rate of 1.69%.

In both the chromatography without standing time and chromatography with standing time, Fraction (Fr.) 0 was fractionated from immediately after injection to the rise of the EPA-E peak, then Fr. 1 to 46were fractionated every 13 seconds, and Fr. 47 was then fractioned for 45 minutes. Methanol was distilled off from the collected fractions using a vacuum evaporator, and C23: 0 methyl ester 1 mg/ml hexane solution was added as an internal standard substance, followed by gas chromatography (GC). The amount of elution of compounds in each fraction was calculated from the area ratio between the GC peak area and the internal standard to select fractions that would provide an EPA-E and DHA-E total content of 86%, and the yield of the product obtained by combining the selected fractions (Fr. 8 to 21 for chromatography without standing time, and Fr. 7 to 25 for chromatography with standing time) and the recovery rate of the EPA-E and DHA-E in the product were determined as follows:

Yield = Weight of the product (g)/load amount (g), $EPA-E$ and $DHA-E$ recovery rate = (Weight of the product (g)×

$EPA-E$ and $DHA-E$ total content (86%)/

(load amount (g)×$EPA-E$ and $DHA-E$ total content (67%).

The conditions used for the GC analysis were as follows. The instrument was a 6890N Network GC System (Agilent) with a DB-WAX 30m×0.25 mm×0.25 μm column. The column temperature was 210° C. The injection temperature was 250° C. with a sprit rate of 1:50 and injection volume of 1 μl. An FID detector at 250° C. was used. A carrier gas of helium with a line speed of 31 cm/minutes was used. The results of yield and recovery rate of EPA-E and DHA-E are shown in Table 10.

TABLE 10

| ODS conc.(Slurry %) | 59 | 59 |
|---|---|---|
| Standing time(min) | 0 | 120 |
| Yield (%) | 72.6 | 77.7 |
| EPA recovery rate (%) | 93.37 | 99.73 |
| DHA recovery rate (%) | 86.75 | 98.50 |

Example 8: Measurement of Median Particle Diameter of Each ODS

The median particle diameter indicates 50% particle size on the volumetric basis and is determined by Laser Scattering Particle Distribution Analyzer LA-920 of Horiba Ltd., using flow cell with 0.2 w/v % sodium hexametaphosphate as dispersing medium. First, 150-200 ml buffer was circulated in a sample bath, then each ODS was added until the laser light transmittance ratio was within 70% and 95%. The amount of ODS was from 70 mg to 120 mg. After the addition, ODS particles was scattered for 1 minute by ultrasonic, then the volume distribution was analyzed, and the median particle diameter was calculated. The results are shown in Table 11.

TABLE 11

| | median particle diameter (μm) | | |
|---|---|---|---|
| ODS-SQ | 48.1 | Example 1-5, 7 | Table 1-5, 9 |
| ODS-B | 54.2 | Example 6 | Table 6 |
| ODS-S20 | 27.5 | Example 6 | Table 7 |
| ODS-S10 | 17.1 | Example 6 | Table 7 |
| ODS-A | 25.8 | Example 6 | Table 8 |
| ODS-Y | 25.9 | Example 6 | Table 6 |

The invention claimed is:

1. A method of purifying one or more compounds by column chromatography comprising:
adding a stationary phase to a column, and
allowing a slurry comprising the stationary phase to settle in the column for a standing time, wherein the stationary phase is a reverse phase silica stationary phase, and the one or more compounds to be purified by column chromatography are selected from fatty acids derived from fish oil or esterified derivatives thereof, proteins and nucleic acids, and wherein chromatography comprises elution with a mobile phase comprising one or more of water, methanol, ethanol, or acetonitrile, and wherein the standing time is about 10 minutes or longer, and wherein a mobile phase is not discharged during the standing time, and loading an analyte comprising the one or more compounds to the column and injecting a mobile phase to purify the one or more compounds, wherein the addition of the stationary phase is conducted by:

a) adding slurry to the column after the slurry is formed by premixing the stationary phase with a mobile phase; or b) adding a mobile phase to the column then adding the stationary phase to the mobile phase in the column.

2. The method of claim 1, wherein the column is under atmospheric pressure during the standing time.

3. The method of claim 1, wherein the standing time is between about 10 minutes to about 15 minutes, about 15 minutes to about 20 minutes, about 20 minutes to about 25 minutes, about 25 minutes to about 30 minutes, about 30 minutes to about 35 minutes, about 35 minutes to about 40 minutes, about 40 minutes to about 45 minutes, about 45 minutes to about 50 minutes, about 50 minutes to about 55 minutes, about 55 minutes to about 60 minutes, about 60 minutes to about 65 minutes, about 65 minutes to about 70 minutes, about 70 minutes to about 75 minutes, about 75 minutes to about 80 minutes, about 80 minutes to about 85 minutes, about 85 minutes to about 90 minutes, about 90 minutes to about 95 minutes, or about 95 minutes to about 100 minutes, about 100 minutes to about 105 minutes, about 105 minutes to about 110 minutes, about 110 minutes to about 115 minutes, about 115 minutes to about 120 minutes.

4. The method of claim 1, wherein the column is an axial compression column.

5. The method of claim 1, wherein the slurry comprises the stationary phase and one or more of water, methanol, ethanol, acetonitrile.

6. The method of claim 5, wherein the slurry comprises methanol.

7. The method of claim 5, wherein the stationary phase comprises an average particle size measured by laser diffraction scattering method of greater than 50 µm, greater than 45 µm, greater than 40 µm, greater than 35 µm, greater than 30 µm, greater than 25 µm, greater than 20 µm, greater than 15 µm, or greater than 10 µm.

8. The method of claim 5, wherein the stationary phase comprises particles of C18.

9. The method of claim 1, wherein the mobile phase comprises methanol.

10. The method of claim 1, wherein the mobile phase comprises an additive selected from one or more of formic acid, ammonium formate, trimethylamine, ammonia, and ammonium hydroxide.

11. The method of claim 1, wherein the mobile phase constitutes a mobile phase gradient.

12. A method of packing a chromatography column in column chromatography comprising:

adding a stationary phase to a column, and allowing a slurry comprising the stationary phase to settle in the column for a standing time, wherein the standing time is about 10 minutes or longer, and wherein a mobile phase is not discharged during the standing time, wherein the stationary phase is a reverse phase silica stationary phase, and the compound to be purified by column chromatography is selected from fatty acids derived from fish oil or esterified derivatives thereof, proteins and nucleic acids, and wherein chromatography comprises elution with a mobile phase comprising one or more of water, methanol, ethanol, or acetonitrile, and wherein the addition of the stationary phase is conducted by:

a) adding the slurry to the column after the slurry is formed by premixing the stationary phase with a mobile phase; or b) adding a mobile phase to the column then adding the stationary phase to the mobile phase in the column.

13. A method of increasing theoretical plate number (N) in a column chromatography comprising:

adding a stationary phase to a column, and allowing a slurry comprising the stationary phase to settle in the column for a standing time, wherein a mobile phase is not discharged during the standing time, performing the column chromatography using the column after the slurry is settled, performing a gas chromatography of a resulting compound obtained by the column chromatography, and calculating the theoretical plate number (N) according to equation (1) below, $$N = \left(\frac{t_R}{\sigma}\right)^2, \qquad (1)$$

wherein $\sigma$ is a standard deviation and $t_R$ is a retention time, wherein the increase in N is relative to a column chromatography without standing time or wherein the increase in N is relative to a slurry that settles for a reduced standing time that is less than the standing time, wherein the stationary phase is a reverse phase silica stationary phase, and the compound to be purified by column chromatography is selected from fatty acids derived from fish oil or esterified derivatives thereof, proteins and nucleic acids, and wherein chromatography comprises elution with a mobile phase comprising one or more of water, methanol, ethanol, or acetonitrile, wherein the standing time is about 10 minutes or longer, and wherein the addition of the stationary phase is conducted by:

a) adding the slurry to the column after the slurry is formed by premixing stationary phase with a mobile phase; or b) adding a mobile phase to the column then adding the stationary phase to the mobile phase.

14. A method of improving symmetry factor of a chromatographic peak in column chromatography comprising:

adding a stationary phase to a column, allowing a slurry to settle in the column for a standing time, wherein a mobile phase is not discharged during the standing time, performing the column chromatography using the column after the slurry is settled, performing a gas chromatography of a resulting compound obtained by the column chromatography, and calculating a symmetry factor according to equation (2) below, $$S = \frac{W_{0.05h}}{2f}, \qquad (2)$$

wherein $W_{0.05h}$ is a peak width at 5% of a height of a chromatographic peak, and f is a peak width of a first half of the chromatographic peak measured as a horizontal distance from a point of a beginning of the chromatographic peak to an apex of a peak amplitude at 5% of the height of the chromatographic peak, and a resulting compound obtained by the column chromatography is selected from fatty acids derived from fish oil or esterified derivatives thereof, proteins and nucleic acids, and wherein chromatography comprises elution with a mobile phase comprising one or more of water, methanol, ethanol, or acetonitrile, and wherein the standing time is about 10 minutes or longer, and wherein the addition of the stationary phase is conducted by:
a) adding the slurry to the column after the slurry is formed by premixing the stationary phase with a mobile phase; or
b) adding a mobile phase to the column then adding the stationary phase to the mobile phase, wherein the improvement comprises decreasing the symmetry factor of the peak to a quantity ≥1, and wherein the decrease is relative to a symmetry factor when the column chromatography comprises a reduced standing time that is absent or less than the standing time and the symmetry factor is >1; or the improvement comprises increasing the symmetry factor of the peak to a quantity ≤1, and wherein the increase is relative to a symmetry factor when a the column chromatography comprises a reduced standing time that is absent or less than the standing time and the symmetry factor is <1, and wherein the slurry comprises a stationary phase that is a reverse phase silica stationary phase, and the compound to be purified by column chromatography is selected from fatty acids derived from fish oil or esterified derivatives thereof, proteins and nucleic acids, and wherein chromatography comprises elution with a mobile phase comprising one or more of water, methanol, ethanol, or acetonitrile.

15. The method of claim 14, further comprising comparing the symmetry factor of the chromatographic peak in the column chromatography with a symmetry factor of a chromatographic peak in a column chromatography obtained by process (I) or (II) below:

(I) a process of obtaining a symmetry factor according to equation (2) for a column chromatography performed without a standing time, comprising
adding a stationary phase to a column,
allowing a slurry to settle in the column for a standing time, wherein a mobile phase is not discharged during the standing time,
performing the column chromatography using the column after the slurry is settled,
performing a gas chromatography of a resulting compound obtained by the column chromatography, and
calculating a symmetry factor according to equation (2) below, $$S = \frac{W_{0.05h}}{2f}, \quad (2)$$

wherein $W_{0.05h}$ is a peak width at 5% of a height of a chromatographic peak, and f is a peak width of a first half of the chromatographic peak measured as a horizontal distance from a point of a beginning of the chromatographic peak to an apex of a peak amplitude at 5% of the height of the chromatographic peak, wherein the addition of the stationary phase is conducted by:
a) adding the slurry to the column after the slurry is formed by premixing the stationary phase with a mobile phase; or
b) adding a mobile phase to the column then adding the stationary phase to the mobile phase, or (II) a process of obtaining a symmetry factor according to equation (2) for a column chromatography performed after a slurry is settled for a reduced standing time that is less than the standing time of about 10 minutes or longer, comprising
adding a stationary phase to a column,
performing the column chromatography using the column after the slurry is settled,
performing a gas chromatography of a resulting compound obtained by the column chromatography, and
calculating a symmetry factor according to equation (2) below, $$S = \frac{W_{0.05h}}{2f}, \quad (2)$$

wherein W0.05h is a peak width at 5% of a height of a chromatographic peak, and f is a peak width of a first half of the chromatographic peak measured as a horizontal distance from a point of a beginning of the chromatographic peak to an apex of a peak amplitude at 5% of the height of the chromatographic peak,
wherein the addition of the stationary phase is conducted by:
a) adding the slurry to the column after the slurry is formed by premixing the stationary phase with a mobile phase; or
b) adding a mobile phase to the column then adding the stationary phase to the mobile phase.

* * * * *